US012686681B2

(12) United States Patent
Ma et al.

(10) Patent No.: US 12,686,681 B2
(45) Date of Patent: Jul. 21, 2026

(54) PROCESS FOR THE PREPARATION OF 2-{3-[3-AMINO-4-(7H-PYRROLO[2,3-D]PYRIMIDIN-4-YL)-1H-PYRAZOL-1-YL]-1-(ISOPROPYLSULFONYL)AZETIDIN-3-YL}ACETONITRILE

(71) Applicant: PrimeGene (Beijing) Co., Ltd., Beijing (CN)

(72) Inventors: Sufeng Ma, Beijing (CN); Junru Han, Beijing (CN); Jin Wang, Beijing (CN); Wei Hu, Beijing (CN); Li Zhu, Beijing (CN)

(73) Assignee: PrimeGene (Beijing) Co., Ltd., Beijing (CN)

( * ) Notice: Subject to any disclaimer, the term of this patent is extended or adjusted under 35 U.S.C. 154(b) by 584 days.

(21) Appl. No.: 18/042,922

(22) PCT Filed: Aug. 25, 2021

(86) PCT No.: PCT/CN2021/114426
§ 371 (c)(1),
(2) Date: Feb. 24, 2023

(87) PCT Pub. No.: WO2022/042577
PCT Pub. Date: Mar. 3, 2022

(65) Prior Publication Data
US 2023/0303578 A1 Sep. 28, 2023

(30) Foreign Application Priority Data
Aug. 25, 2020 (CN) ........................ 202010865137.9

(51) Int. Cl.
*C07D 487/04* (2006.01)

(52) U.S. Cl.
CPC .................................. *C07D 487/04* (2013.01)

(58) Field of Classification Search
CPC .................................................. C07D 487/04
USPC ......................................................... 544/280
See application file for complete search history.

(56) References Cited

FOREIGN PATENT DOCUMENTS

| | | |
|---|---|---|
| CN | 105777754 A | 7/2016 |
| CN | 107513067 A | 12/2017 |

(Continued)

OTHER PUBLICATIONS

First Office Action for Chinese Patent No. 2020108651379 mailed on Dec. 9, 2023 with English translation (11 pages).
Extended European search report dated Aug. 22, 2024 received in European Patent Application No. 21860412.2.
Second Office Action dated Feb. 9, 2024 received in Chinese Patent Application No. 202010865137.9.
International Search Report issued on Nov. 17, 2021 for International Patent Application No. PCT/CN2021/114426 (3 pages).
First Indian Office Action issued on Aug. 9, 2023 for Indian Patent Application No. 20233701692.3 (6 pages).

*Primary Examiner* — Douglas M Willis
(74) *Attorney, Agent, or Firm* — Scully, Scott, Murphy & Presser, P.C.

(57) ABSTRACT

The present application relates to a preparation method for a pyrrolopyrimidine compound, comprising: obtaining a compound 3 from a compound 2, obtaining a compound 4P2 from the compound 3, and obtaining a pyrrolopyrimidine compound of formula I by removing a protecting group from the compound 4P2. The preparation method of the present application has the advantages of simple operation, mild reaction conditions and high yield, avoids the problems of low yield and a large amount of impurities and difficult separation of same in original routes, reduces production costs, and is suitable for industrial production. Furthermore, the product yield of each step is high, and basically reaches about 80%, and even the yield of some steps can reach 90% or more.

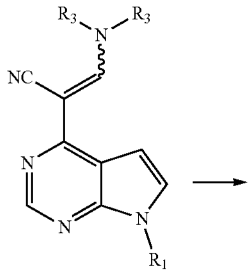

2

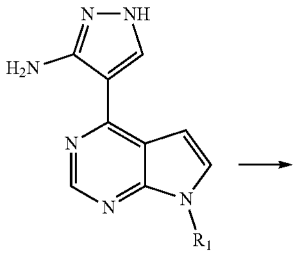

3

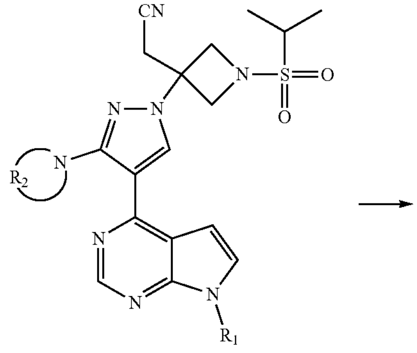

4P2

(Continued)

-continued

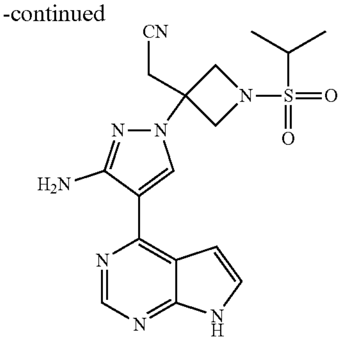

I

2 Claims, No Drawings

(56) References Cited

FOREIGN PATENT DOCUMENTS

| | | | |
|---|---|---|---|
| CN | 109867675 | A | 6/2019 |
| CN | 109867676 | A | 6/2019 |
| EP | 3473625 | B1 | 6/2021 |
| IN | 201941040504 | A | 4/2021 |
| WO | 2010039939 | A1 | 4/2010 |
| WO | 2016095805 | A1 | 6/2016 |
| WO | 2022042577 | A1 | 3/2022 |

PROCESS FOR THE PREPARATION OF 2-{3-[3-AMINO-4-(7H-PYRROLO[2,3-D]PYRIMIDIN-4-YL)-1H-PYRAZOL-1-YL]-1-(ISOPROPYLSULFONYL)AZETIDIN-3-YL}ACETONITRILE

CROSS REFERENCE TO RELATED APPLICATIONS

This application is the U.S. national phase of International Patent Application No. PCT/CN2021/114426, filed on Aug. 25, 2021, which claims priority to Chinese Patent Application No. 202010865137.9, filed on Aug. 25, 2020, the disclosures of which are incorporated herein by reference in their entirety.

TECHNICAL FIELD

The present application pertains to the field of chemical drug synthesis, and relates to a method for synthesizing pyrrolopyrimidine compounds and intermediate process products thereof.

BACKGROUND

JAK kinases belong to the family of intracellular non-receptor tyrosine kinases, which play an important role in the cytokine-receptor signaling pathway through the interaction with signal transducer and activator of transcription (STAT). The JAK family includes four members, JAK1, JAK2, JAK3 and TYK2, among which JAK1, JAK2 and TYK2 are widely present in various tissue cells, while JAK3 only exists in the bone marrow and lymphatic system. Seven members of the STAT family, i.e., STAT1-STAT6 (5a/5b), have been identified. JAK kinases mediate the signal transduction of most cytokines in cells, such as interleukins (ILs) and interferons (IFNs), and different receptors can activate different subtypes of JAK kinases, thus exhibiting differentiated biological functions. The JAK-STAT signaling pathway is an important intracellular signal transduction pathway in the process of growth, activation, differentiation, apoptosis and function exertion of various cells, and is related to the pathogenesis of various inflammatory diseases, such as rheumatoid arthritis, atopic dermatitis and psoriasis. In the past decade, several JAK inhibitors have been approved for marketing, such as Ruxolitinib from Incyte/Novartis, Tofacitinib from Pfizer, Baricitinib from Incyte/Lilly, and Upadacitinib from AbbVie, for use in the treatment of diseases such as myelofibrosis, rheumatoid arthritis, psoriatic arthritis, and ulcerative colitis. In addition, clinical trials are being undergone for many other indications, such as psoriasis, atopic dermatitis, and systemic lupus erythematosus.

Small-molecule drugs with pyrrolopyrimidine structures have been one of the key structures for developing JAK inhibitors in recent years. Tofacitnib, Ruxolitinib, and Baricitinib all have pyrrolopyrimidine-type molecular structures, and many other JAK small molecules with such structures have been reported. The patent for invention, CN201711248509.8, discloses a series of JAK inhibitors, including the compound, 2-{3-[3-amino-4-(7H-pyrrolo[2,3-d]pyrimidin-4-yl)-1H-pyrazol-1-yl]-1-(isopropylsulfonyl)azetidin-3-yl}acetonitrile, represented by the following formula I:

I

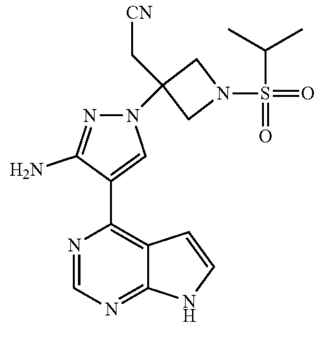

The method for preparing compound I as disclosed in the patent No. CN201711248509.8 is shown below:

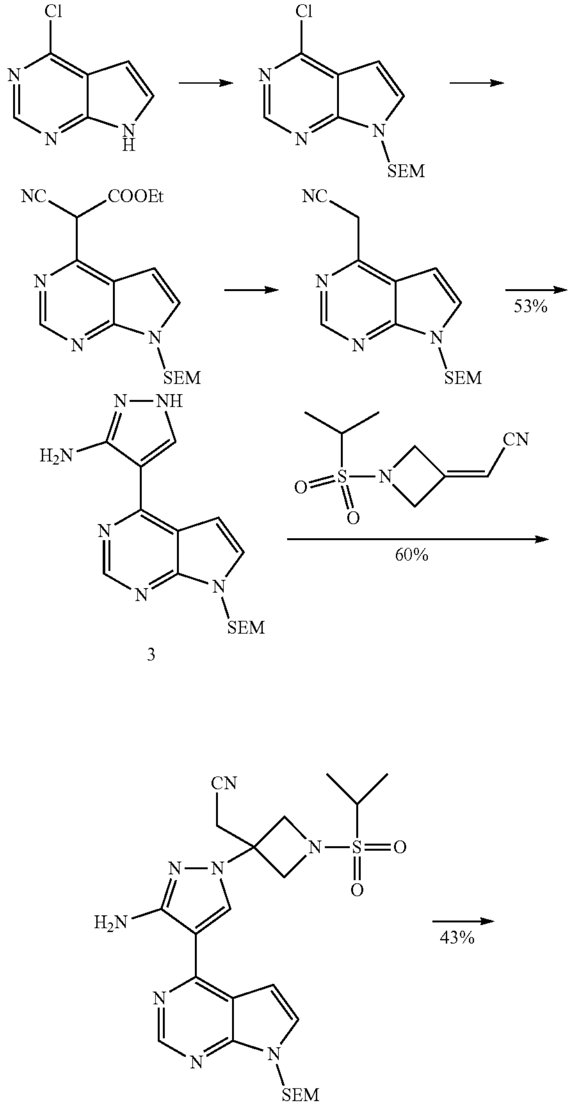

-continued

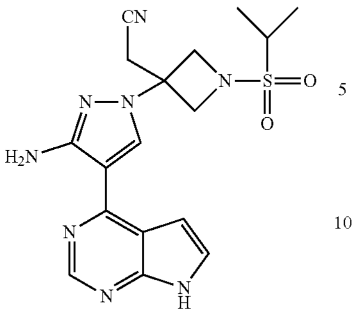

(I)

The yields of the last three steps in this route are all low, and can only reach about 40-60%, even after further optimization, there is no obvious improvement; moreover, this method has the problems of a large amount of impurities and difficult separation of the same. Therefore, this route has a relatively high production cost, and is not suitable for commercial production.

SUMMARY

The present application further provides a new method for preparing compound I, which has the characteristics of simple operation, environmental friendliness, high synthesis yield and excellent product quality.

The present application provides a method for preparing a pyrrolopyrimidine compound of formula I, comprising:

obtaining compound 3 from compound 2, obtaining compound 4P2 from compound 3, and obtaining the pyrrolopyrimidine compound of formula I by removing a protecting group from compound 4P2:

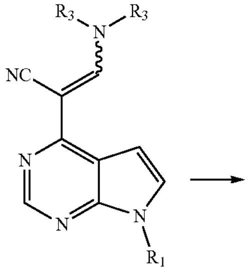

2

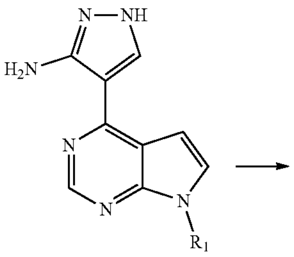

3

-continued

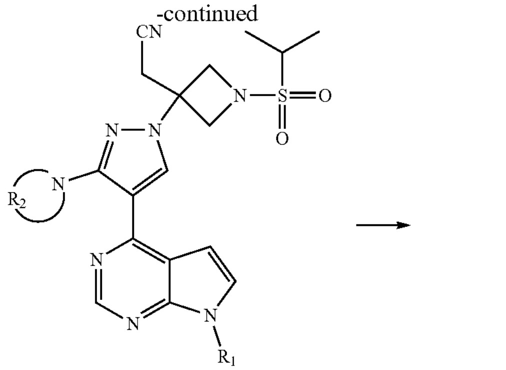

4P2

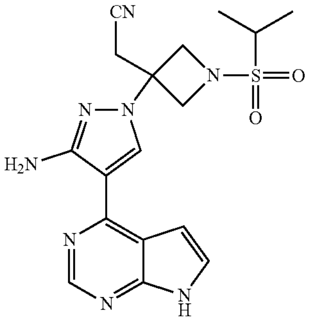

I wherein, R1 and R2 are selected from hydrogen or an amino protecting group, and R3 is selected from hydrogen or a $C_1$-$C_4$ alkyl group, or two R3 groups, together with the N atom to which they are attached, form a C3- to C8-membered ring.

In some embodiments, obtaining compound 3 from compound 2 comprises reacting compound 2 with a hydrazine compound and an optional acetal compound to prepare said compound 3.

In some embodiments, said hydrazine compound may be in the form of an aqueous solution of hydrazine, an organic solution of hydrazine, or a salt of hydrazine.

In some embodiments, the molar ratio of said compound 2 to said hydrazine compound is in a range of from 1:1.0 to 1:50.0.

In some embodiments, the acetal compound is selected from N,N-di(C1-C4 alkyl)formamide di(C1-C4 alkyl)acetals or 5- to 6-membered azaheterocycle-N-formamide di(C1-C4 alkyl)acetals (for example, N,N-dimethylformamide dimethyl acetal, N,N-dimethylformamide diethyl acetal, N,N-diethylformamide dimethyl acetal, N,N-diethylformamide diethyl acetal, pyrrolidine-N-formamide dimethyl acetal, pyrrolidine-N-formamide diethyl acetal, piperidine-N-formamide dimethyl acetal, piperidine-N-formamide diethyl acetal, morpholine-N-formamide dimethyl acetal, morpholine-N-formamide diethyl acetal, or the like).

In some embodiments, the reaction solvent is selected from N,N-dimethylformamide, N,N-dimethylacetamide, N,N-diethylformamide, N,N-diethylacetamide, N-methylpyrrolidone, ethyl acetate, methanol, ethanol, isopropanol, tert-butanol, n-butanol, tetrahydrofuran, methyltetrahydrofuran, acetonitrile, or a mixed solvent thereof.

In some embodiments, obtaining compound 4P2 from compound 3 comprises:

subjecting the 3-position amino group of the pyrazole ring of compound 3 to amino protection to obtain compound 3P;

subjecting compound 3P and compound SM2 to Michael addition reaction in the presence of a base to obtain compound 4P1; and subjecting compound 4P1 to removal and transformation of the R4 group to obtain compound 4P2;

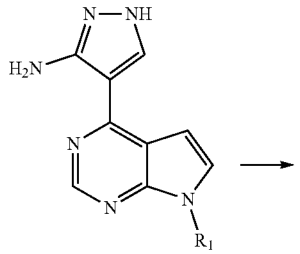

3

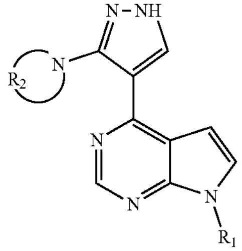

3P

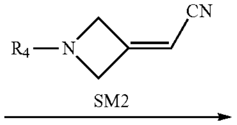

SM2

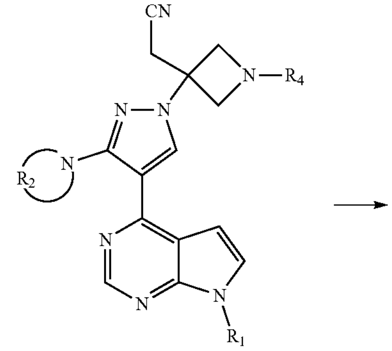

4P1

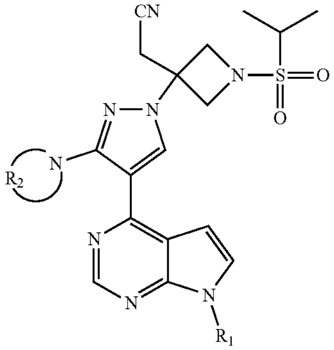

4P2 wherein, R1 and R2 are as defined above, and R4 is hydrogen or an amino protecting group other than isopropylsulfonyl.

In some embodiments, subjecting the 3-position amino group of the pyrazole ring of compound 3 to amino protection to obtain compound 3P comprises:

subjecting compound 3 with the unprotected 3-position amino group to amino protection by using a cyclic imide protecting agent, wherein, the cyclic imide protecting agent is selected from the group consisting of succinic anhydride, methylsuccinic anhydride, 3,3-dimethylsuccinic anhydride, 3,4-dimethylsuccinic anhydride, 3-bromotetrahydrofuran-2,5-dione, phthalic anhydride, tetrahydrophthalic anhydride, 1,2-cyclohexanedicarboxylic anhydride, 4-methyltetrahydrophthalic anhydride, methylhexahydrophthalic anhydride, 4-methylphthalic anhydride, 3-methylphthalic anhydride, 3,4-dimethylphthalic anhydride, 3-methoxyphthalic anhydride, 4-methoxyphthalic anhydride, 4-chlorophthalic anhydride, 3,4-difluorophthalic anhydride, 3,6-difluorophthalic anhydride, maleic anhydride, and glutaric anhydride;

the molar ratio of said cyclic imide protecting agent to compound 3 may be in a range of from 0.8:1 to 1.3:1; and the reaction solvent may be selected from toluene, xylene, or a mixture thereof.

In some embodiments, obtaining compound 4P2 from compound 3 comprises:

subjecting compound 3 and compound SM2 to Michael addition reaction in the presence of a base to obtain compound 4;

subjecting the 3-position amino group of the pyrazole ring of compound 4 to amino protection to obtain compound 4P1; and subjecting compound 4P1 to removal and transformation of the R4 group to obtain compound 4P2;

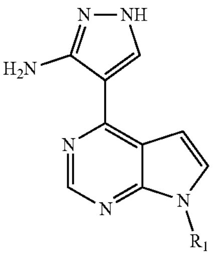

3

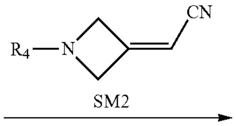

SM2

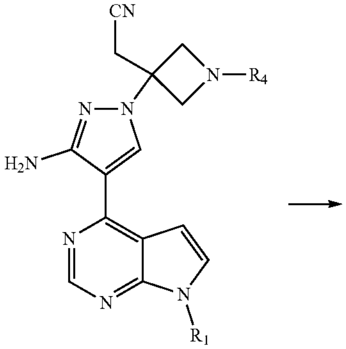

4

-continued

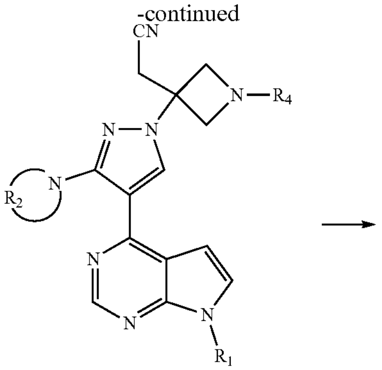

4P1

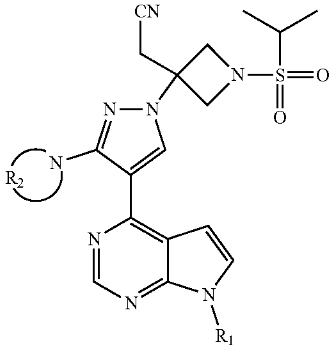

4P2 wherein, R1 and R2 are as defined above, and R4 is hydrogen or an amino protecting group other than isopropylsulfonyl.

In some embodiments, subjecting the 3-position amino group of the pyrazole ring of compound 4 to amino protection to obtain compound 4P1 comprises:

subjecting compound 4 with the unprotected 3-position amino group to amino protection by using a cyclic imide protecting agent, wherein, the cyclic imide protecting agent is selected from the group consisting of succinic anhydride, methylsuccinic anhydride, 3,3-dimethylsuccinic anhydride, 3,4-dimethylsuccinic anhydride, 3-bromotetrahydrofuran-2,5-dione, phthalic anhydride, tetrahydrophthalic anhydride, 1,2-cyclohexanedicarboxylic anhydride, 4-methyltetrahydrophthalic anhydride, methylhexahydrophthalic anhydride, 4-methylphthalic anhydride, 3-methylphthalic anhydride, 3,4-dimethylphthalic anhydride, 3-methoxyphthalic anhydride, 4-methoxyphthalic anhydride, 4-chlorophthalic anhydride, 3,4-difluorophthalic anhydride, 3,6-difluorophthalic anhydride, maleic anhydride, and glutaric anhydride;

the molar ratio of said cyclic imide protecting agent to compound 4 may be in a range of from 0.8:1 to 1.3:1; and the reaction solvent may be selected from toluene, xylene, or a mixture thereof.

In some embodiments, subjecting compound 4P1 to removal and transformation of the R4 group to obtain compound 4P2 comprises:

removing the R4 protecting group from compound 4P1 to obtain compound 5 or a salt thereof, and reacting compound 5 with an isopropylsulfonyl reagent to obtain compound 4P2;

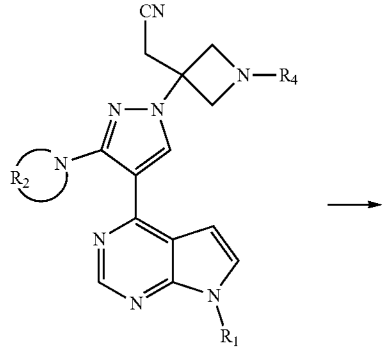

4P1

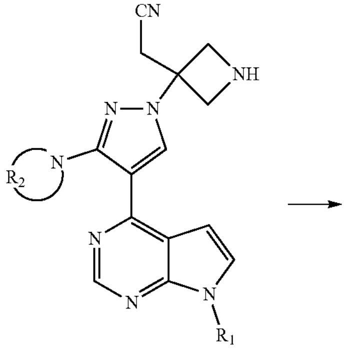

5

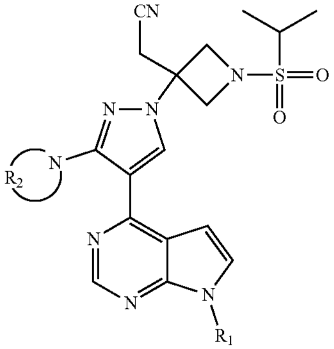

4P2 wherein, R1, R2, and R4 are as defined above.

In some embodiments, said isopropylsulfonyl reagent is selected from the group consisting of isopropylsulfonyl chloride, isopropylsulfonyl bromide, isopropylsulfonic acid, methyl isopropylsulfonate, ethyl isopropylsulfonate, and isopropyl isopropylsulfonate.

The molar ratio of said isopropylsulfonyl reagent to compound 5 may be in a range of from 0.5:1 to 1.5:1, such as from 0.8:1 to 12.0:1, and such as from 1.0:1 to 1.1:1.

The reaction solvent may be selected from N,N-dimethylformamide, N,N-dimethylacetamide, N-methylpyrrolidone, methyl tert-butyl ether, isopropyl ether, ethyl acetate, isopropyl acetate, tetrahydrofuran, methyltetrahydrofuran, acetonitrile, toluene, methylene chloride, chloroform, chlorobenzene, or a mixed solvent thereof. Preferably, the reaction solvent is N,N-dimethylformamide, N,N-dimethylacetamide, N-methylpyrrolidone, dichloromethane, acetonitrile, methyl tert-butyl ether, isopropyl ether, ethyl acetate, tetrahydrofuran, or methyltetrahydrofuran; more preferably, the solvent is dichloromethane, tetrahydrofuran, or acetonitrile.

The reaction temperature may be in a range of from −20° C. to 80° C., preferably from −20° C. to 0° C., from 0° C. to 30° C., from 50° C. to 60° C., or from 75° C. to 80° C.

In some embodiments, obtaining compound 4P2 from compound 3 comprises:

subjecting the 3-position amino group of the pyrazole ring of compound 3 to amino protection to obtain compound 3P; and subjecting compound 3P and compound SM1, 2-[1-(isopropylsulfonyl)azetidin-3-ylidene]acetonitrile, to Michael addition reaction in the presence of a base to obtain compound 4P2;

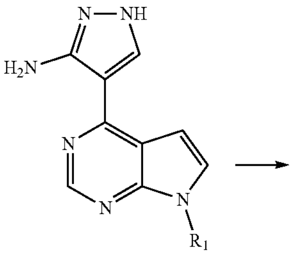

3

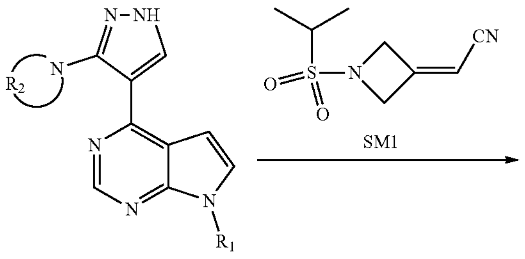

3P

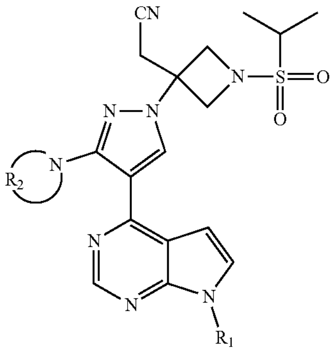

4P2 wherein, R1 and R2 are as defined above.

In some embodiments, obtaining compound 4P2 from compound 3 comprises:

subjecting compound 3 and compound SM1, 2-[1-(isopropylsulfonyl)azetidin-3-ylidene]acetonitrile, to Michael addition reaction in the presence of a base to obtain compound 4P3; and subjecting the 3-position amino group of the pyrazole ring of compound 4P3 to amino protection to obtain compound 4P2;

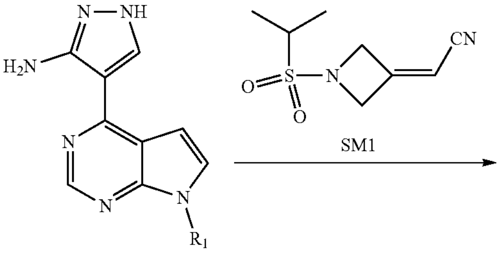

3

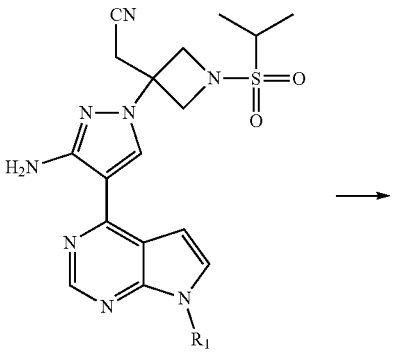

4P3

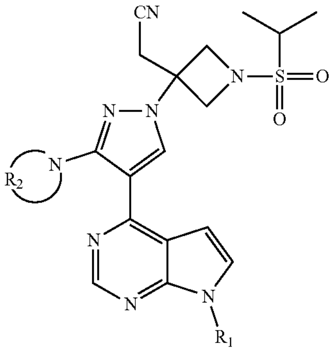

4P2 wherein, R1 and R2 are as defined above.

In some embodiments, in said Michael addition reaction, the base is selected from the group consisting of sodium hydroxide, potassium hydroxide, sodium carbonate, potassium carbonate, cesium carbonate, sodium methoxide, potassium methoxide, sodium hydride, sodium tert-butoxide, potassium tert-butoxide, tetramethylguanidine, triethylamine, diisopropylethylamine, 1,8-diazabicyclo[5.4.0]undec-7-ene (DBU), 1,5-diazabicyclo[4.3.0]non-5-ene (DBN), 1,5,7-triazabicyclo[4.4.0]dec-5-ene (TBD), and 7-methyl-1,5,7-triazabicyclo[4.4.0]dec-5-ene (MTBD); wherein said base is preferably sodium hydride, tetramethylguanidine, 1,8-diazabicyclo[5.4.0]undec-7-ene (DBU), or 1,5-diazabicyclo[4.3.0]non-5-ene (DBN).

The molar ratio of the base to the reactant compound may be in a range of from 0.05:1 to 5.0:1.

The reaction solvent may be selected from N,N-dimethylformamide, N,N-dimethylacetamide, N,N-diethylformamide, N,N-diethylacetamide, N-methylpyrrolidone, dimethyl sulfoxide, methanol, ethanol, isopropanol, tetrahydrofuran, methyltetrahydrofuran, acetonitrile or a mixed solvent thereof, wherein N,N-dimethylformamide, N,N-dimethylacetamide, N-methylpyrrolidone, dimethyl sulfoxide, or acetonitrile is preferred.

In some embodiments, obtaining the pyrrolopyrimidine compound of formula I by removing a protecting group from compound 4P2 comprises:

reacting compound 4P2 with an elimination reagent to remove the protecting group to obtain said pyrrolopyrimidine compound of formula I;

wherein, the elimination reagent may be selected from trifluoroacetic acid, trifluoromethanesulfonic acid, boron trifluoride, lithium tetrafluoroborate, sodium tetrafluoroborate, potassium tetrafluoroborate, ammonia gas, ammonia water, ethylenediamine, propylenediamine, ethanolamine, propanolamine, hydrazine, hydrazine hydrate, hydrazine salts, organic solutions of hydrazine, or a combination thereof;

the molar ratio of the elimination reagent to compound 4P2 may be in a range of from 1.0:1 to 50.0:1; and the reaction solvent may be selected from N,N-dimethylformamide, N,N-dimethylacetamide, N-methylpyrrolidone, dimethyl sulfoxide, dichloromethane, chloroform, methyl tert-butyl ether, isopropyl ether, tetrahydrofuran, methyltetrahydrofuran, acetonitrile, methanol, ethanol, isopropanol, or a mixed solvent thereof.

In some embodiments, obtaining the pyrrolopyrimidine compound of formula I by removing a protecting group from compound 4P2 comprises:

removing the R1 protecting group from compound 4P2 to obtain compound 6; and obtaining said pyrrolopyrimidine compound of formula I from compound 6;

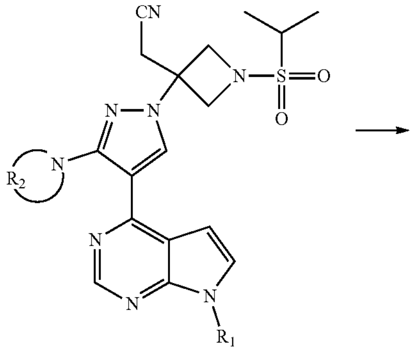

4P2

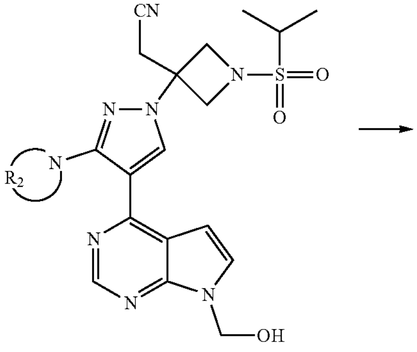

6

-continued

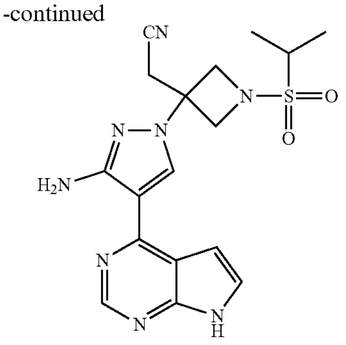

I wherein, R1 and R2 are as defined above.

In some embodiments, when R1 is an amino protecting group, it may be selected from hydroxymethyl, benzyloxycarbonyl (Cbz), 2,2,2-trichloroethoxycarbonyl (Troc), 2-(trimethylsilyl)ethoxycarbonyl (Teoc), 2-(4-trifluoromethylbenzenesulfonyl)ethoxycarbonyl (TSC), tert-butoxycarbonyl (Boc), 1-adamantyloxycarbonyl (Adoc), 2-adamantylcarbonyl (2-Adoc), 2,4-dimethylpent-3-yloxycarbonyl (Doc), methoxymethyl, tert-butoxymethyl (Bum), benzyloxymethyl (Bom), 2-tetrahydropyranyl, 2-(trimethylsilyl)ethoxymethyl (SEM) or N-pivaloyloxymethyl (POM), trityl (Tr), trimethylsilyl (Tms), triphenylsilyl (Ts), benzenesulfonyl, p-toluenesulfonyl, methanesulfonyl, ethylsulfonyl, p-nitrobenzenesulfonyl, acetyl, or trifluoroacetyl.

R2, together with the amino group, may form a cyclic imide protecting group, which is selected from the group consisting of succinimide, methylsuccinimide, 2,2-dimethylsuccinimide, 2,3-dimethylsuccinimide, 2-bromosuccinimide, phthalimide, tetrahydrophthalimide, 1,2-cyclohexanedicarboximide, 4-methyltetrahydrophthalimide, methylhexahydrophthalimide, 4-methylphthalimide, 3-methylphthalimide, 3,4-dimethylphthalimide, 3-methoxyphthalimide, 4-methoxyphthalimide, 4-chlorophthalimide, 3,4-difluorophthalimide, 3,6-difluorophthalimide, maleimide, and glutarimide groups. The above-mentioned groups may be represented by the following structural formulas:

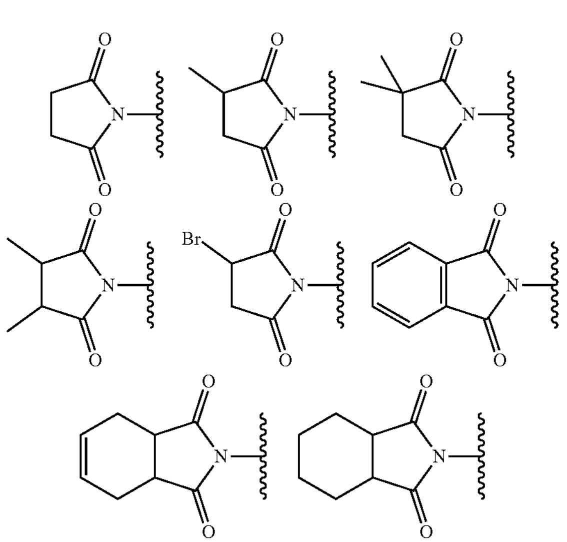

-continued

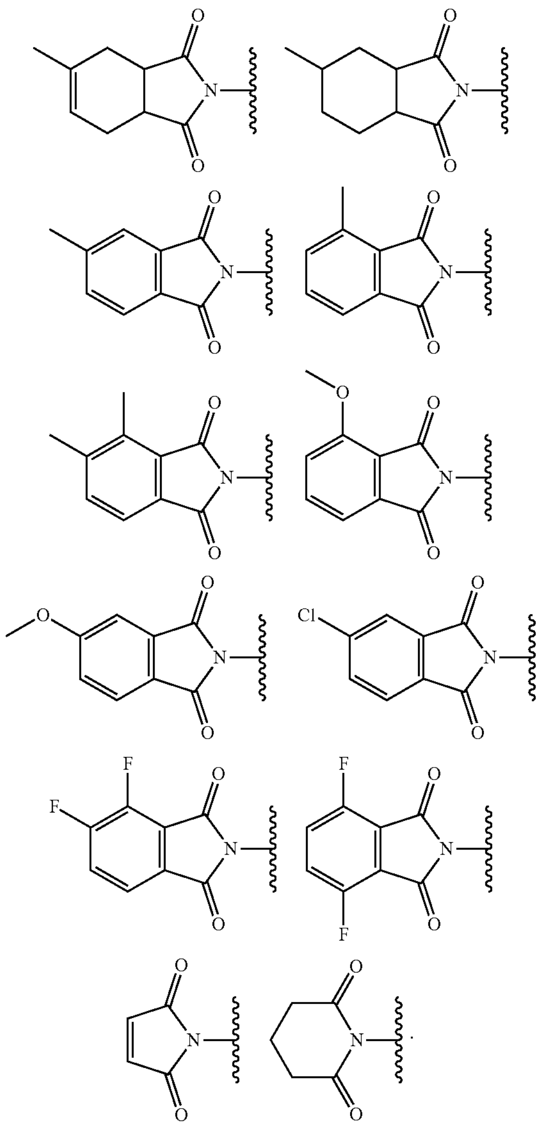

R3 may be selected from H, methyl, ethyl, propyl, isopropyl, butyl, or isobutyl, or 2 R3 groups, together with the N atom to which they are attached, form a tetrahydropyrrole ring, a piperidine ring, or a morpholine ring.

R4 may be selected from the group consisting of hydrogen, isopropylsulfonyl, benzyloxycarbonyl (Cbz), 2,2,2-trichloroethoxycarbonyl (Troc), 2-(trimethylsilyl)ethoxycarbonyl (Teoc), 2-(4-trifluoromethylbenzenesulfonyl) ethoxycarbonyl (TSC), tert-butoxycarbonyl (Boc), 1-adamantyloxycarbonyl (Adoc), 2-adamantylcarbonyl (2-Adoc), 2,4-dimethylpent-3-yloxycarbonyl (Doc), methoxymethyl, tert-butoxymethyl (Bum), benzyloxymethyl (Bom), 2-tetrahydropyranyl, (THP), 2-(trimethylsilyl) ethoxymethyl (SEM), N-pivaloyloxymethyl (POM), trityl (Tr), trimethylsilyl (Tms), triphenylsilyl (Ts), benzenesulfonyl, p-toluenesulfonyl, methanesulfonyl, ethylsulfonyl, p-nitrobenzenesulfonyl, and acetyl.

In another aspect, the present application relates to intermediate compound 4P1, intermediate compound 5 or intermediate compound 6 having the formula

4P1

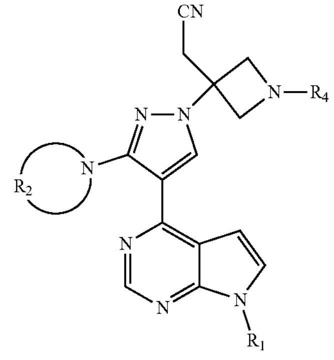

5

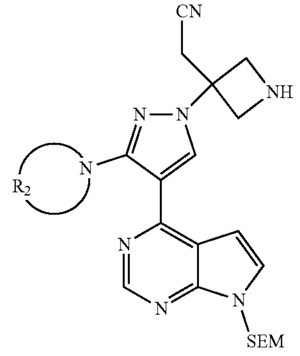

6

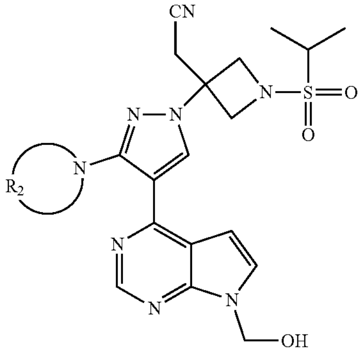

wherein, R1 and R2 are hydrogen or an amino protecting group, R4 is hydrogen, an amino protecting group, or isopropylsulfonyl, and SEM refers to 2-(trimethylsilyl) ethoxymethyl.

Specifically, these compounds may be selected from the group consisting of the following Compounds 4a, 4b, 4c, 4d, 4e, 4f, 5a, 5b, 5c, 6a, 6b, and 6c:

4a
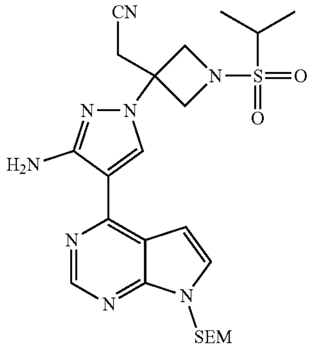
4b
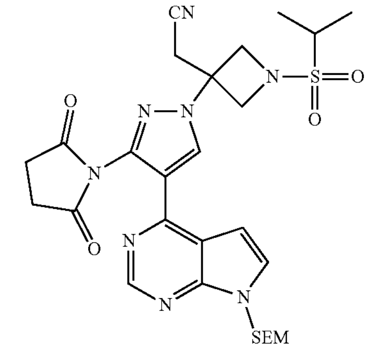
4c
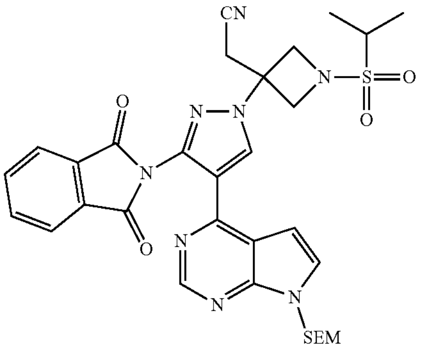
4d
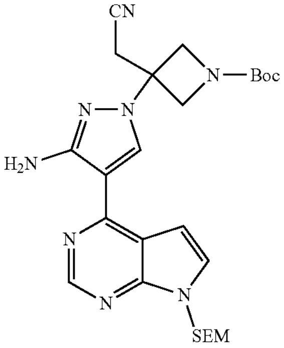
-continued
4e
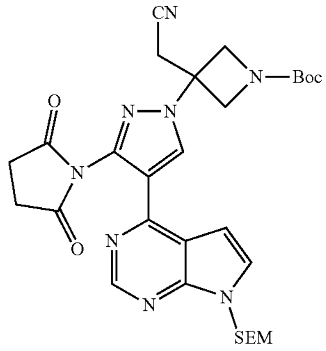
4f
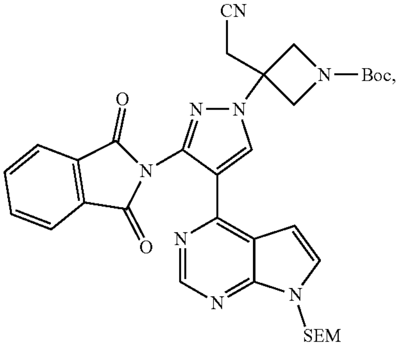
5a
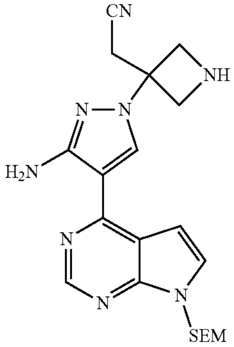
5b
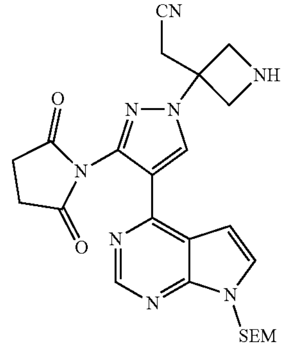

-continued

5c

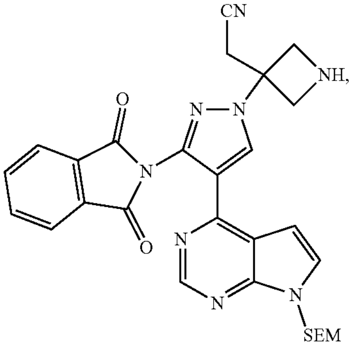

6a

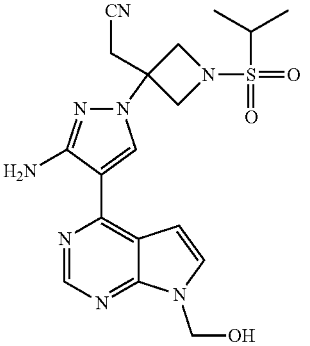

6b

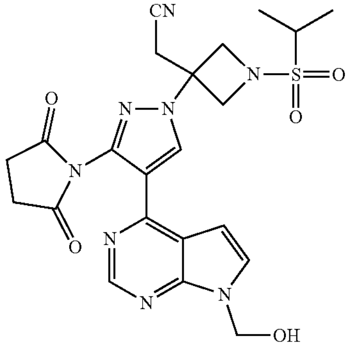

6c

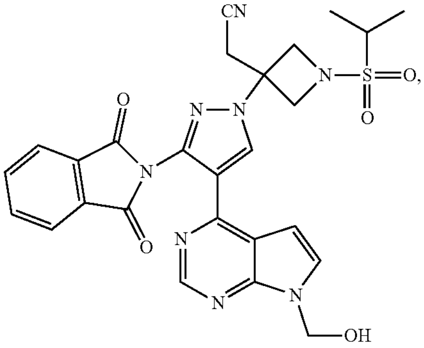

wherein SEM refers to 2-(trimethylsilyl)ethoxymethyl; and Boc refers to tert-butoxycarbonyl.

The preparation method of the present application has the advantages of simple operation, mild reaction conditions and high yield, avoids the problems of low yield, a large amount of impurities and difficult separation of the same in existing preparation methods, reduces production cost, and is suitable for industrial production. Furthermore, the product yield of each step is high, and basically reaches about 80%, and even the yield of some steps can reach 90% or more.

DETAILED DESCRIPTION

In one aspect, the present application provides a method for preparing a pyrrolopyrimidine compound of formula I, comprising:

obtaining compound 3 from compound 2, obtaining compound 4P2 from compound 3, and obtaining the pyrrolopyrimidine compound of formula I by removing a protecting group from compound 4P2:

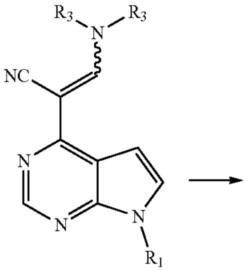

2

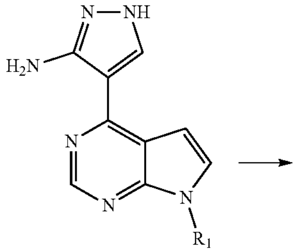

3

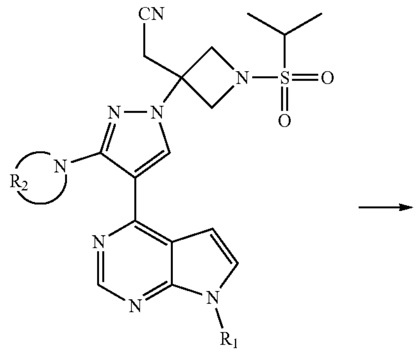

4P2

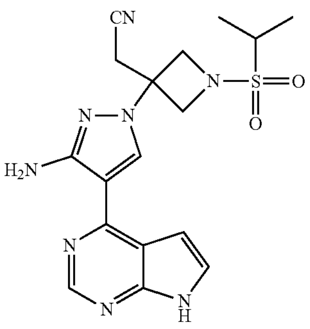

I wherein, R1 and R2 are selected from hydrogen or an amino protecting group, and R3 is selected from hydrogen or C1-C4 alkyl, or two R3 groups, together with the N atom to which they are attached, form a C3- to C8-membered ring.

The method of the present invention uses compound 2 as a starting material to obtain compound I with a high yield. The preparation processes are described respectively below.

In embodiments of the present application, R1 may be selected from hydrogen or an amino protecting group, and is further limited to be hydrogen, hydroxymethyl, benzyloxycarbonyl (Cbz), 2,2,2-trichloroethoxycarbonyl (Troc), 2-(trimethylsilyl)ethoxycarbonyl (Teoc), 2-(4-trifluoromethylbenzenesulfonyl)ethoxycarbonyl (TSC), tert-butoxycarbonyl (Boc), 1-adamantyloxycarbonyl (Adoc), 2-adamantylcarbonyl (2-Adoc), 2,4-dimethylpent-3-yloxycarbonyl (Doc), methoxymethyl, tert-butoxymethyl (Bum), benzyloxymethyl (Bom), 2-tetrahydropyranyl, (THP), 2-(trimethylsilyl)ethoxymethyl (SEM), N-pivaloyloxymethyl (POM), trityl (Tr), trimethylsilyl (Tms), triphenylsilyl (Ts), benzenesulfonyl, p-toluenesulfonyl, methanesulfonyl, ethylsulfonyl, p-nitrobenzenesulfonyl, acetyl, or trifluoroacetyl; preferably, 2-(trimethylsilyl)ethoxymethyl (SEM), trityl (Tr), benzyloxymethyl (Bom), methoxymethyl, hydroxymethyl, or benzyloxycarbonyl (Cbz).

In embodiments of the present application, R2, together with the amino group, forms a cyclic imide protecting group as defined above, which is preferably a succinimide or phthalimide group.

In embodiments of the present application, R3 may be selected from hydrogen, methyl, ethyl, propyl, isopropyl, butyl, tert-butyl, or the like. Alternatively, two R3 groups, together with the N atom, may form a C3- to C8-membered ring, for example, a tetrahydropyrrole ring, a piperidine ring, a morpholine ring, or the like.

In an embodiment of the present application, R4 may be selected from hydrogen, isopropylsulfonyl, benzyloxycarbonyl (Cbz), 2,2,2-trichloroethoxycarbonyl (Troc), 2-(trimethylsilyl)ethoxycarbonyl (Teoc), 2-(4-trifluoromethylbenzenesulfonyl)ethoxycarbonyl (TSC), tert-butoxycarbonyl (Boc), 1-adamantyloxycarbonyl (Adoc), 2-adamantylcarbonyl (2-Adoc), 2,4-dimethylpent-3-yloxycarbonyl (Doc), methoxymethyl, tert-butoxymethyl (Bum), benzyloxymethyl (Bom), 2-tetrahydropyranyl, (THP), 2-(trimethylsilyl)ethoxymethyl (SEM) or N-pivaloyloxymethyl (POM), trityl (Tr), trimethylsilyl (Tms), triphenylsilyl (Ts), benzenesulfonyl, p-toluenesulfonyl, methanesulfonyl, ethylsulfonyl, p-nitrobenzenesulfonyl, or acetyl.

I. Obtaining Compound 3

In some embodiments, obtaining compound 3 from compound 2 comprises reacting compound 2 with a hydrazine compound and an optional acetal compound to prepare said compound 3.

In some embodiments, said hydrazine compound is selected from the group consisting of an aqueous solution of hydrazine, an organic solution of hydrazine, and a salt of hydrazine. In some embodiments, the hydrazine compound has a reaction ratio (molar ratio, based on 1.0 eq of compound 2) in a range of from 1.0 eq to 50.0 eq, preferably a reaction ratio in a range of from 2.0 eq to 20.0 eq, more preferably in a range of from 3.0 eq to 10.0 eq.

Reacting compound 2 with a hydrazine compound to prepare compound 3 may be carried out in the presence of an organic solvent. In some embodiments, the reaction solvent may be selected from N,N-dimethylformamide, N,N-dimethylacetamide, N,N-diethylformamide, N,N-diethylacetamide, N-methylpyrrolidone, ethyl acetate, methanol, ethanol, isopropanol, tert-butanol, n-butanol, tetrahydrofuran, methyltetrahydrofuran, acetonitrile, or a mixed solvent thereof, preferably, the reaction solvent is N,N-dimethylformamide, N,N-dimethylacetamide, N-methylpyrrolidone, methanol, ethanol, isopropanol, or n-butanol.

In some embodiments, the reaction of compound 2 with a hydrazine compound may also be carried out in the presence of an optional acetal compound to improve the reaction yield. "Optional acetal compound" means that an acetal compound may or may not be present during the reaction. The inventors have found that, when there is no acetal compound, the reaction of compound 2 with a hydrazine compound can also obtain the desired compound 3, but there will be about 10-20% of undesired by-products. However, when an acetal compound is used during the reaction, these undesired by-products can be efficiently converted into the desired compound 3, which can greatly improve the yield of the target compound 3. In some embodiments, the acetal compound is selected from N,N-di(C1-C4 alkyl) formamide di(C1-C4 alkyl)acetals or 5- to 6-membered azaheterocycle-N-formamide di(C1-C4 alkyl)acetals, for example, N,N-dimethylformamide dimethyl acetal, N,N-dimethylformamide diethyl acetal, N,N-diethylformamide dimethyl acetal, N,N-diethylformamide diethyl acetal, pyrrolidine-N-formamide dimethyl acetal, pyrrolidine-N-formamide diethyl acetal, piperidine-N-formamide dimethyl acetal, piperidine-N-formamide diethyl acetal, morpholine-N-formamide dimethyl acetal, morpholine-N-formamide diethyl acetal, or the like. These 5- to 6-membered azaheterocycle-N-formamide di(C1-C4 alkyl) acetals may be, for example, methyl or ethyl acetals having the following formulas:

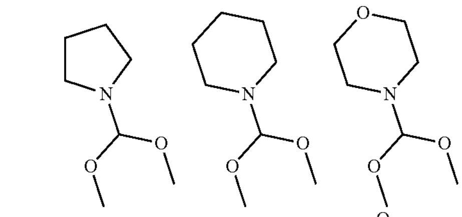
,
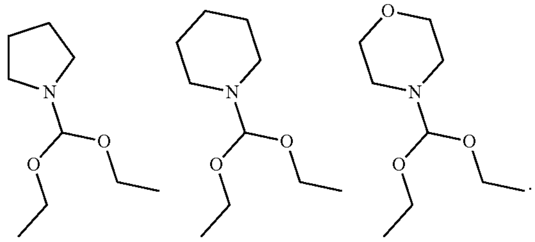
.

In some embodiments, the acetal compound has a reaction ratio (molar ratio, based on 1.0 eq of compound 2) in a range of from 0.1 to 0.3 eq, from 0.3 to 0.5 eq, from 0.5 to 1.0 eq, or from 1.0 eq to 5.0 eq.

II. Obtaining Compound 4P2

Obtaining compound 4P2 from compound 3 may be carried out according to the following steps:

1. Compound 3 undergoes amino protection, reacts with SM2 (an amino protecting group other than isopropylsulfonyl), removes R4, and forms a sulfonamide to obtain compound 4P2.

This process comprises the following steps of:

subjecting the 3-position amino group of the pyrazole ring of compound 3 to amino protection to obtain compound 3P;

subjecting compound 3P and compound SM2 to Michael addition reaction in the presence of a base to obtain compound 4P1; and subjecting compound 4P1 to removal and transformation of the R4 group to obtain compound 4P2;

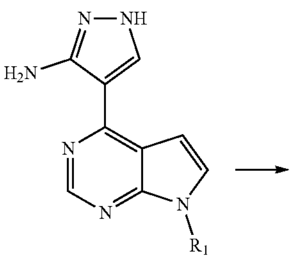

3

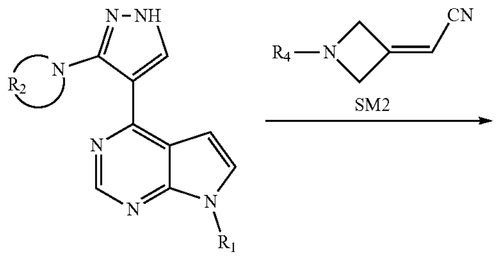

SM2

3P

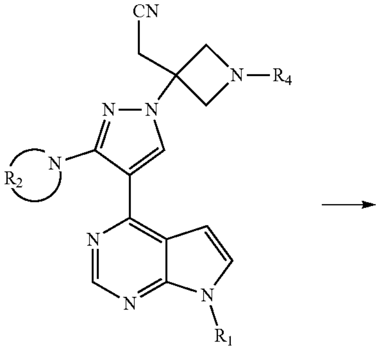

4P1

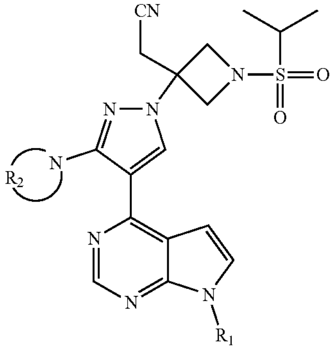

4P2 wherein, R1 and R2 are as defined above, and R4 is hydrogen or an amino protecting group other than isopropylsulfonyl.

In some embodiments, the amino protection of compound 3 with the 3-position unprotected amino group is carried out by using a cyclic imide protecting agent. The cyclic imide protecting agent may be selected from the group consisting of succinic anhydride, methylsuccinic anhydride, 3,3-dimethylsuccinic anhydride, 3,4-dimethylsuccinic anhydride, 3-bromotetrahydrofuran-2,5-dione, phthalic anhydride, tetrahydrophthalic anhydride, 1,2-cyclohexanedicarboxylic anhydride, 4-methyltetrahydrophthalic anhydride, methylhexahydrophthalic anhydride, 4-methylphthalic anhydride, 3-methylphthalic anhydride, 3,4-dimethylphthalic anhydride, 3-methoxyphthalic anhydride, 4-methoxyphthalic anhydride, 4-chlorophthalic anhydride, 3,4-difluorophthalic anhydride, 3,6-difluorophthalic anhydride, maleic anhydride, and glutaric anhydride. In some embodiments, the cyclic imide protecting agent has a reaction ratio (molar ratio, based on 1.0 eq of compound 3) in a range of from 0.8 to 1.3 eq, preferably from 1.0 to 1.2 eq, more preferably from 1.0 eq to 1.1 eq; the molar ratio is in a range of from 0.8:1 to 1.3:1. The reaction may be carried out in a reaction solvent. The reaction solvent may be selected from toluene, xylene, or a mixed solvent thereof, preferably toluene.

In said Michael addition reaction, the base may be selected from the group consisting of sodium hydroxide, potassium hydroxide, sodium carbonate, potassium carbonate, cesium carbonate, sodium methoxide, potassium methoxide, sodium hydride, sodium tert-butoxide, potassium tert-butoxide, tetramethylguanidine, triethylamine, diisopropylethylamine, 1,8-diazabicyclo[5.4.0]undec-7-ene (DBU), 1,5-diazabicyclo[4.3.0]-non-5-ene (DBN), 1,5,7-triazabicyclo[4.4.0]dec-5-ene (TBD), and 7-methyl-1,5,7-triazabicyclo[4.4.0]dec-5-ene (MTBD); wherein said base is preferably sodium hydride, tetramethylguanidine, 1,8-diazabicyclo[5.4.0]undec-7-ene (DBU), or 1,5-diazabicyclo[4.3.0]non-5-ene (DBN). In some embodiments, the base has a reaction ratio (molar ratio, based on 1.0 eq of compound 3P) in a range of from 0.05 eq to 5.0 eq, preferably, a reaction ratio in a range of from 0.1 eq to 3.0 eq, and more preferably, a ratio in a range of from 0.1 to 1.0 eq.

In some embodiments, the Michael addition reaction may be carried out in the presence of a reaction solvent. The reaction solvent may be selected from N,N-dimethylformamide, N,N-dimethylacetamide, N,N-diethylformamide, N,N-diethylacetamide, N-methylpyrrolidone, dimethyl sulfoxide, methanol, ethanol, isopropanol, tetrahydrofuran, methyltetrahydrofuran, acetonitrile, or a mixed solvent thereof, wherein N,N-dimethylformamide, N,N-dimethylacetamide, N-methylpyrrolidone, dimethyl sulfoxide, or acetonitrile is preferred.

Compound 4P1 is subjected to elimination and transformation of the R4 functional group to prepare compound 4P2. In some embodiments, for the compound wherein R4 is a group other than isopropylsulfonyl, subjecting compound 4P1 to removed and transformation of the R4 group to obtain compound 4P2 comprises:

removing the protecting group R4 from compound 4P1 to obtain compound 5 or a salt thereof, and reacting compound 5 with an isopropylsulfonyl reagent to obtain compound 4P2;

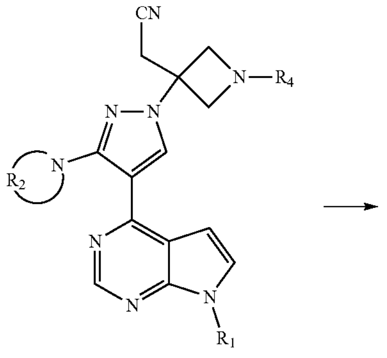

4P1

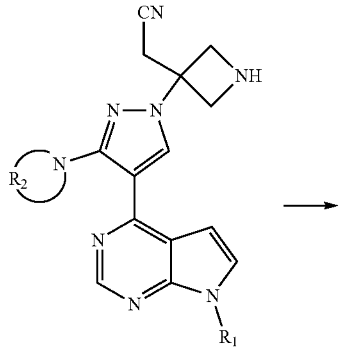

5

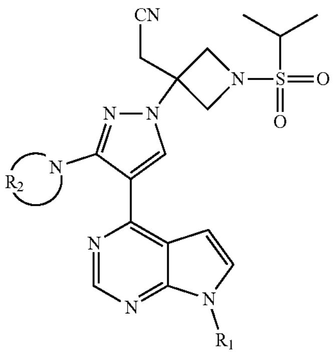

4P2 wherein, R1, R2, and R4 are as defined above.

The reaction of removing the amino protecting group R4 from compound 4P1 under the action of a reagent to produce compound 5 or a salt thereof. Different removal reagents are used according to different R4 amino protecting groups. R4 may be selected from benzyloxycarbonyl (Cbz), 2,2,2-trichloroethoxycarbonyl (Troc), 2-(trimethylsilyl)ethoxycarbonyl (Teoc), 2-(4-trifluoro methylbenzenesulfonyl)ethoxycarbonyl (TSC), tert-butoxycarbonyl (Boc), 1-adamantyloxycarbonyl (Adoc), 2-adamantylcarbonyl (2-Adoc), or 2,4-dimethylpent-3-yloxycarbonyl (Doc). The corresponding protecting group removal methods can be achieved by conventional methods in the art, which methods can be a one-step reaction or a multi-step reaction, such as but not limited to, those in "Greene's Protective Groups in Organic Synthesis", 5th Edition, published by Wiley, and in "Protecting Group Chemistry" published by Chemical Industry Press. In some embodiments, the salt of compound 5 includes sulfate, phosphate, hydrochloride, hydrobromide, formate, acetate, oxalate, succinate, fumarate, maleate, oxalate, malonate, and the like.

Compound 5 reacts with an isopropylsulfonyl reagent to prepare compound 4P2. The isopropylsulfonyl reagent used may be selected from the group consisting of isopropylsulfonyl chloride, isopropylsulfonyl bromide, isopropylsulfonic acid, methyl isopropylsulfonate, ethyl isopropylsulfonate, and isopropyl isopropylsulfonate. In some embodiments, the isopropylsulfonyl reagent used has a ratio (molar ratio, based on 1.0 eq of compound 5) in a range of from 0.5 eq to 1.5 eq, preferably from 0.8 eq to 12.0 eq, and further preferably from 1.0 eq to 1.1 eq. The reaction of compound 5 and an isopropylsulfonyl reagent to prepare compound 4P2 may be carried out in a reaction solvent. The reaction solvent may be selected from N,N-dimethylformamide, N,N-dimethylacetamide, N-methylpyrrolidone, methyl tert-butyl ether, isopropyl ether, ethyl acetate, isopropyl acetate, tetrahydrofuran, methyltetrahydrofuran, acetonitrile, toluene, methylene chloride, chloroform, chlorobenzene, or a mixed solvent thereof; preferably, the reaction solvent is N,N-dimethylformamide, N,N-dimethylacetamide, N-methylpyrrolidone, dichloromethane, acetonitrile, methyl tert-butyl ether, isopropyl ether, ethyl acetate, tetrahydrofuran, or methyltetrahydrofuran; further preferably, the solvent is dichloromethane, tetrahydrofuran, or acetonitrile. Compound 4P2 is prepared by reacting compound 5 with the isopropylsulfonyl reagent at a reaction temperature which may be selected from a range of from −20 to 80° C., preferably from −20 to 0° C., from 0 to 30° C., from 50 to 60° C., or from 75 to 80° C.

To sum up, compound 4P2 is prepared by reacting compound 2 with a hydrazine compound to prepare compound 3, subjecting compound 3 to amino protection to prepare compound 3P, reacting compound 3P with compound SM2 to prepare compound 4P1, and subjecting compound 4P1 to transformation of the R4 functional group. The scheme is as follows:

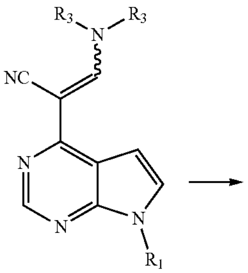

2

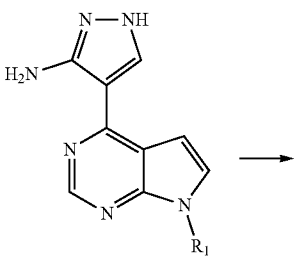

3

-continued

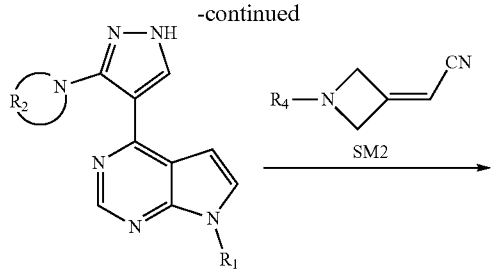

3P

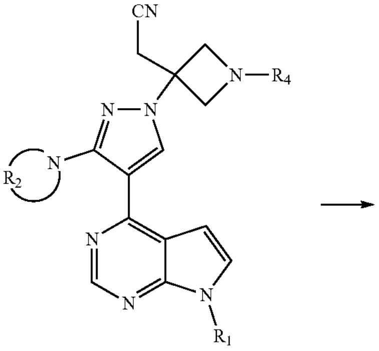

4P1

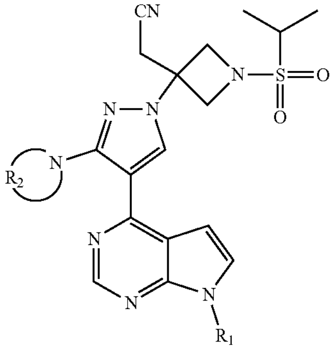

4P2

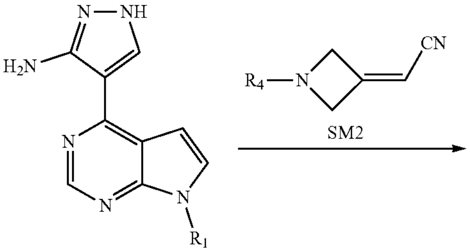

3

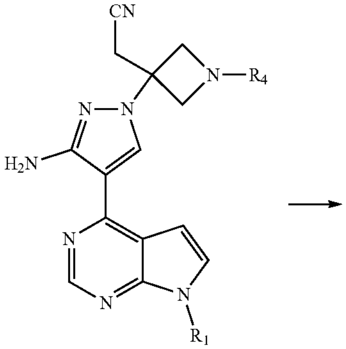

4

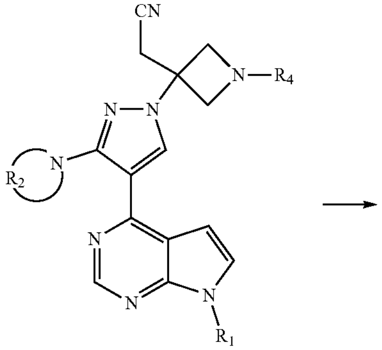

4P1

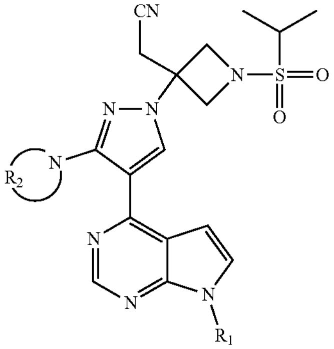

4P2

For the process of obtaining compound I from compound 4P2, reference can be made to the following description.

2. Compound 3 reacts with SM2 (an amino-protecting group other than isopropylsulfonyl), undergoes amino protection, removes R4, and forms a sulfonamide to obtain compound 4P2.

In some embodiments, obtaining compound 4P2 from compound 3 comprises:

subjecting compound 3 and compound SM2 to Michael addition reaction in the presence of a base to obtain compound 4;

subjecting the 3-position amino group of the pyrazole ring of compound 4 to amino protection to obtain compound 4P1; and subjecting compound 4P1 to removal and transformation of the R4 group to obtain compound 4P2;

wherein, R1 and R2 are as defined above, and R4 is hydrogen or an amino protecting group other than isopropylsulfonyl.

For the process of subjecting the 3-position amino group of the pyrazole ring of compound 4 to amino protection to obtain compound 4P1, reference can be made to the process of subjecting compound 3 with the 3-position unprotected amino group to amino protection by using a cyclic imide protecting agent as mentioned above. The cyclic imide protecting agent may be selected from the group consisting of succinic anhydride, methylsuccinic anhydride, 3,3-dimethylsuccinic anhydride, 3,4-dimethylsuccinic anhydride, 3-bromotetrahydrofuran-2,5-dione, phthalic anhydride, tetrahydrophthalic anhydride, 1,2-cyclohexanedicarboxylic anhydride, 4-methyltetrahydrophthalic anhydride, methylhexahydrophthalic anhydride, 4-methylphthalic anhydride, 3-methylphthalic anhydride, 3,4-dimethylphthalic anhydride, 3-methoxyphthalic anhydride, 4-methoxyphthalic anhydride, 4-chlorophthalic anhydride, 3,4-difluorophthalic anhydride, 3,6-difluorophthalic anhydride, maleic anhydride, and glutaric anhydride. In some embodiments, the cyclic imide protecting agent has a reaction ratio (molar ratio, based on 1.0 eq of compound 4) in a range of from 0.8 to 1.3 eq, preferably a range of from 1.0 to 1.2 eq, more preferably a range of from 1.0 eq to 1.1 eq; the molar ratio is in a range of from 0.8:1 to 1.3:1. The reaction may be carried out in a reaction solvent. The reaction solvent may be selected from toluene, xylene, or a mixed solvent thereof, preferably toluene.

For the Michael addition reaction of compound 3 and compound SM2 in the presence of a base, reference can be made to the above description about the Michael addition reaction process. In said Michael addition reaction, the base may be selected from the group consisting of sodium hydroxide, potassium hydroxide, sodium carbonate, potassium carbonate, cesium carbonate, sodium methoxide, potassium methoxide, sodium hydride, sodium tert-butoxide, potassium tert-butoxide, tetramethylguanidine, triethylamine, diisopropylethylamine, 1,8-diazabicyclo[5.4.0]undec-7-ene (DBU), 1,5-diazabicyclo[4.3.0]non-5-ene (DBN), 1,5,7-triazabicyclo[4.4.0]dec-5-ene (TBD), 7-methyl-1,5,7-triazabicyclo[4.4.0]dec-5-ene (MTBD); wherein said base is preferably sodium hydride, tetramethylguanidine, 1,8-diazabicyclo[5.4.0]undec-7-ene (DBU), or 1,5-diazabicyclo[4.3.0]non-5-ene (DBN). In some embodiments, the base has a reaction ratio (molar ratio, based on 1.0 eq of compound 3) in a range of from 0.05 eq to 5.0 eq, preferably, a reaction ratio in a range of from 0.1 eq to 3.0 eq, and more preferably, a ratio in a range of from 0.1 to 1.0 eq.

In some embodiments, the Michael addition reaction may be carried out in the presence of a reaction solvent. The reaction solvent may be selected from N,N-dimethylformamide, N,N-dimethylacetamide, N,N-diethylformamide, N,N-diethylacetamide, N-methylpyrrolidone, dimethyl sulfoxide, methanol, ethanol, isopropanol, tetrahydrofuran, methyltetrahydrofuran, acetonitrile, or a mixed solvent thereof, wherein N,N-dimethylformamide, N,N-dimethylacetamide, N-methylpyrrolidone, dimethyl sulfoxide, or acetonitrile is preferred.

Compound 4P1 is subjected to removal and transformation of the R4 group to obtain compound 4P2. For this process, reference can be made to the above description, which will not be repeated here.

To sum up, compound 4P2 is prepared by cyclizing compound 2 with a hydrazine compound to prepare compound 3, reacting compound 3 with compound SM2 to prepare compound 4, subjecting compound 4 to amino protection to prepare compound 4P1, and subjecting compound 4P1 to transformation of the R4 functional group. The scheme is as follows:

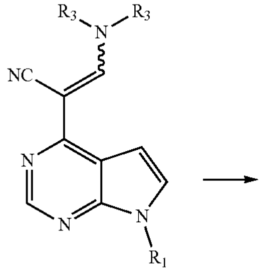

2

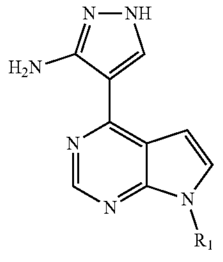

3

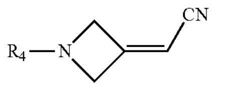

SM2

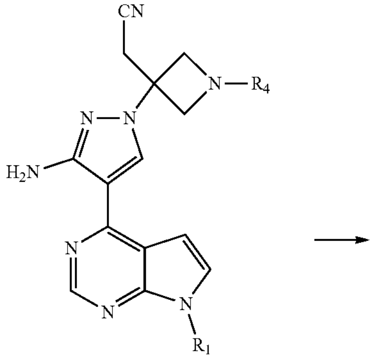

4

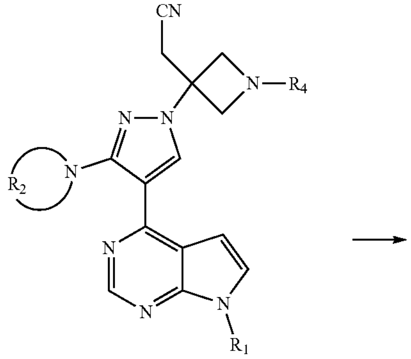

4P1

-continued

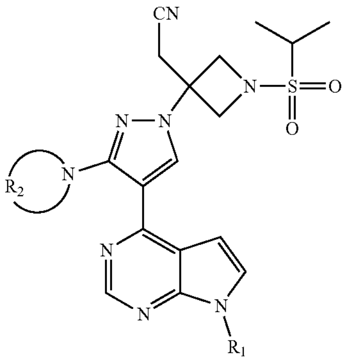

4P2

For the process of obtaining compound I from compound 4P2, reference can be made to the following description.

3. Compound 3 is subjected to amino protection and reacts with SM2 (isopropylsulfonyl) to obtain compound 4P2.

In some embodiments, obtaining compound 4P2 from compound 3 comprises:

- subjecting the 3-position amino group of the pyrazole ring of compound 3 to amino protection to obtain compound 3P; and
- subjecting compound 3P and compound SM1, 2-[1-(isopropylsulfonyl)azetidin-3-ylidene]acetonitrile, to Michael addition reaction in the presence of a base to obtain compound 4P2;

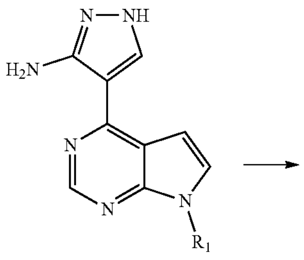

3

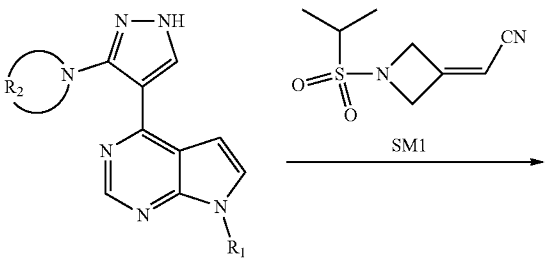

3P

-continued

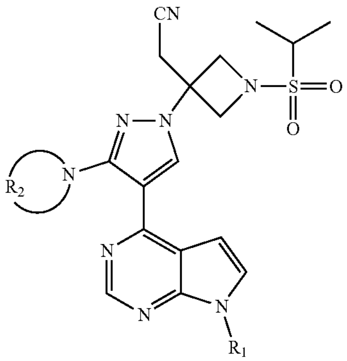

4P2 wherein, R1 and R2 are as defined above.

4. Compound 3 reacts with SM2 (isopropylsulfonyl) and then is subjected to amino protection to obtain compound 4P2.

In some embodiments, obtaining compound 4P2 from compound 3 comprises:

- subjecting compound 3 and compound SM1, 2-[1-(isopropylsulfonyl)azetidin-3-ylidene]acetonitrile, to Michael addition reaction in the presence of a base to obtain compound 4P3; and
- subjecting the 3-position amino group of the pyrazole ring of compound 4P3 to amino protection to obtain compound 4P2;

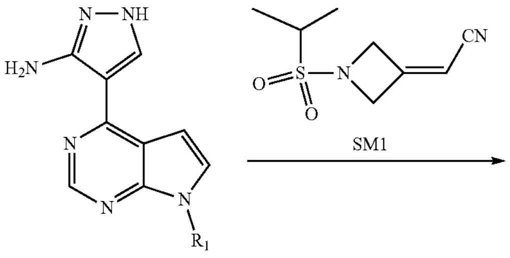

3

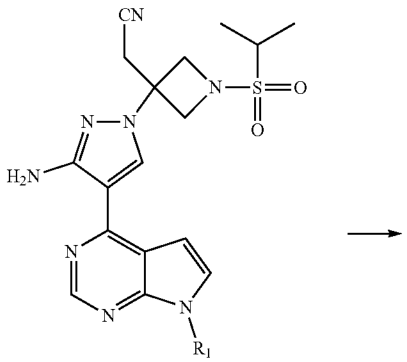

4P3

-continued

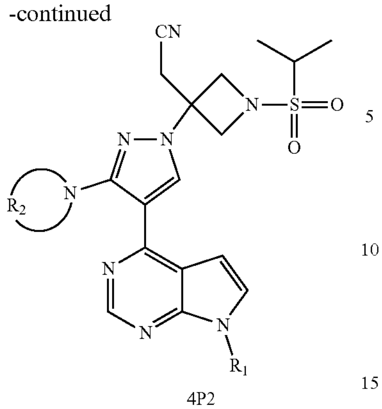

4P2 wherein, R1 and R2 are as defined above.

To sum up, when R4=isopropylsulfonyl, compound 4P2 can be obtained by directly reacting compound 3 or 3P with compound SM1 (2-[1-(isopropylsulfonyl)azetidin-3-ylidene]acetonitrile).

The above two processes can be described by the following scheme.

description about the amino protection reaction process, which will not be repeated here.

III. Obtaining the Pyrrolopyrimidine Compound of Formula I

1. One-Step Removal Method

In some embodiments, obtaining the pyrrolopyrimidine compound of formula I by removing a protecting group from compound 4P2 comprises:

reacting compound 4P2 with an elimination reagent to remove the protecting group to obtain said pyrrolopyrimidine compound of formula I.

In some embodiments, the elimination reagent (protecting group removal reagent) includes trifluoroacetic acid, trifluoromethanesulfonic acid, boron trifluoride, lithium tetrafluoroborate, sodium tetrafluoroborate, potassium tetrafluoroborate, ammonia gas, ammonia water, ethylenediamine, propylenediamine, ethanolamine, propanolamine, hydrazine, hydrazine hydrate, hydrazine salts, organic solutions of hydrazine, or a combination thereof. In some embodiments, the molar ratio of the elimination reagent to compound 4P2 is in a range of from 1.0:1 to 50.0:1, preferably from 1.0:1 to 10.0:1.

The reaction solvent is selected from N,N-dimethylformamide, N,N-dimethylacetamide, N-methylpyrrolidone,

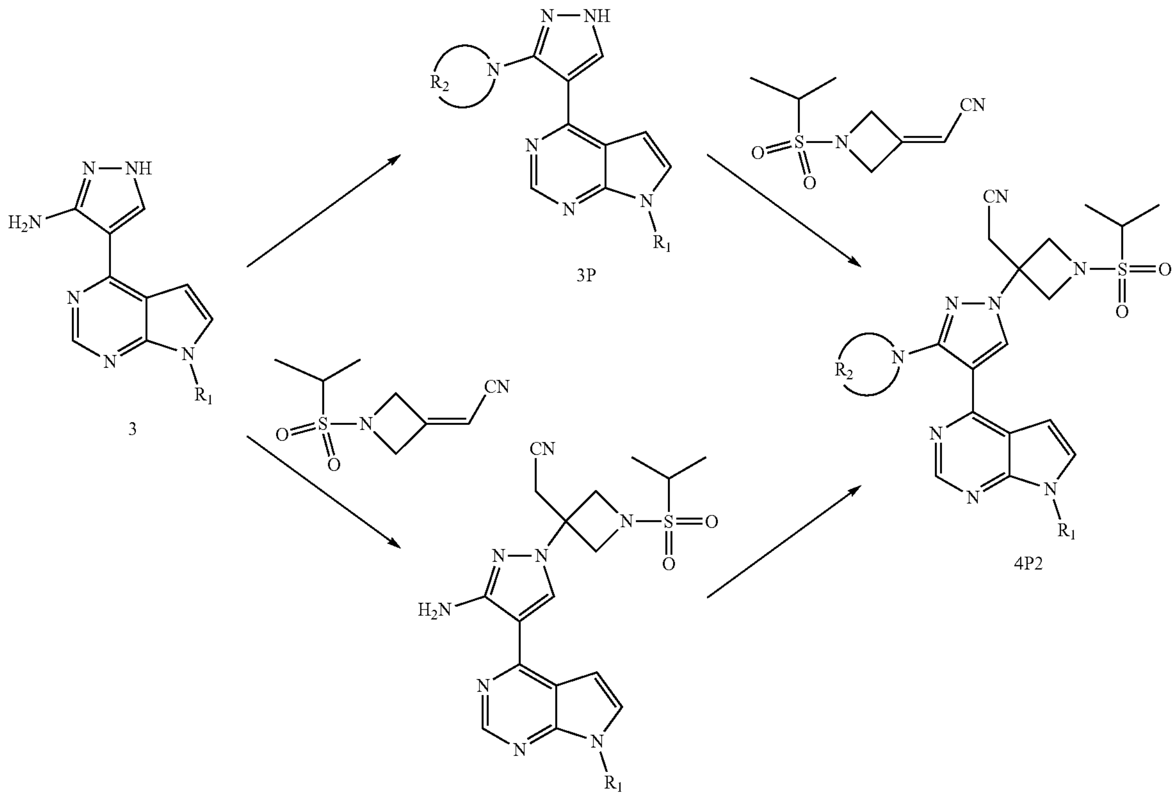

3

3P

4P3

4P2

For the Michael addition reaction in the above reaction processes, reference can also be made to the above description about the Michael addition reaction process, which will not be repeated here.

Similarly, for the process of subjecting the 3-position amino group of the pyrazole ring of compound 3 or 4P3 to amino protection, reference can also be made to the above description about the amino protection reaction process, which will not be repeated here.

dimethyl sulfoxide, dichloromethane, chloroform, methyl tert-butyl ether, isopropyl ether, tetrahydrofuran, methyltetrahydrofuran, acetonitrile, methanol, ethanol, isopropanol, or a mixed solvent thereof. Preferably, the reaction solvent is dichloromethane, tetrahydrofuran, N,N-dimethylformamide, dimethyl sulfoxide, methanol, ethanol, isopropanol, or acetonitrile.

2. Two-Step Removal Method

Compound 4P2 is subjected to removal of part of the R1 protecting groups under the action of a reagent to produce compound 6 with a hydroxymethyl group, which can be isolated or can be directly used for the next reaction step without isolation to prepare compound I.

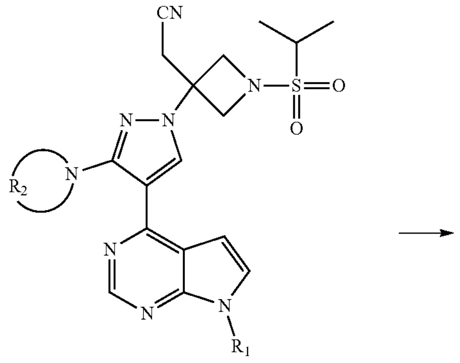

4P2

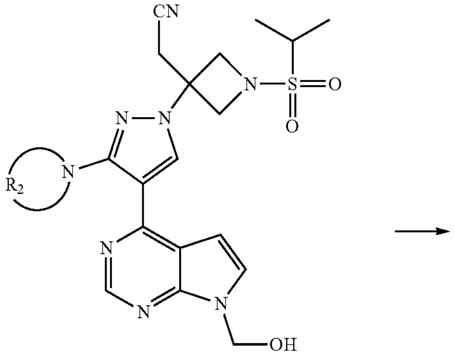

6

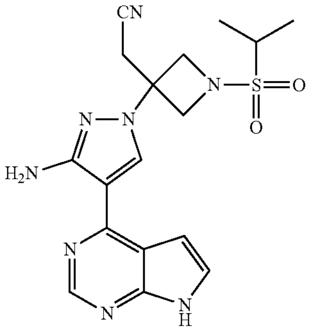

I

In some embodiments, obtaining the pyrrolopyrimidine compound of formula I by removing a protecting group from compound 4P2 comprises:

obtaining compound 6 by removing the R1 protecting group from compound 4P2; and obtaining said pyrrolopyrimidine compound of formula I from compound 6;

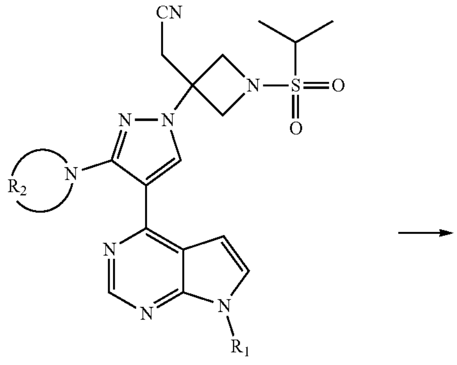

4P2

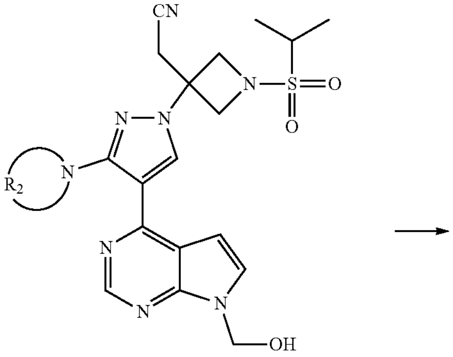

6

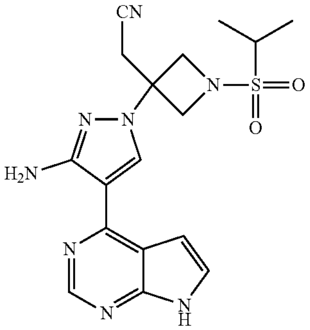

I wherein, R1 and R2 are as defined above.

In the above process, 1) preparing compound 6 from compound 4P2 is included. The reaction reagent may be selected from the group consisting of trifluoroacetic acid, trifluoromethanesulfonic acid, boron trifluoride, lithium tetrafluoroborate, sodium tetrafluoroborate, and potassium tetrafluoroborate. In some embodiments, the reaction reagent has an amount ratio (molar ratio, based on 1.0 eq of compound 4P2) in a range of from 1.0 eq to 10.0 eq, preferably from 2.0 eq to 8.0 eq, more preferably from 3.0 eq to 5.0 eq. The reaction may be carried out in the presence of a reaction solvent. The reaction solvent may be selected from N,N-dimethylformamide, N,N-dimethylacetamide, N-methylpyrrolidone, dimethyl sulfoxide, dichloromethane, chloroform, methyl tert-butyl ether, isopropyl ether, tetrahydrofuran, methyltetrahydrofuran, acetonitrile, methanol, ethanol, isopropanol, or a mixed solvent thereof. Preferably, the reaction solvent is dichloromethane, acetonitrile, or tetrahydrofuran. In some embodiments, the reaction temperature may be selected from a range of from −20 to 80° C., preferably from −20 to 0° C., from 0 to 30° C., or from 45 to 50° C.

The above process also includes 2) preparing compound I from compound 6. The reaction reagent used in this step may be selected from ammonia gas, ammonia water, ethylenediamine, propylenediamine, ethanolamine, propanolamine, hydrazine, hydrazine hydrate, hydrazine salts, organic solutions of hydrazine, or a combination thereof. The amount ratio (molar ratio, based on 1.0 eq of compound 6) of the reaction reagent ranges from 1.0 eq to 50.0 eq, preferably from 3.0 eq to 10.0 eq, further preferably from 3.0 eq to 5.0 eq. The reaction may be carried out in the presence of a reaction solvent. The reaction solvent may be selected from N,N-dimethylformamide, N,N-dimethylacetamide, N-methylpyrrolidone, dimethyl sulfoxide, methanol, ethanol, isopropanol, methyl tert-butyl ether, isopropyl ether, tetrahydrofuran, methyl tetrahydrofuran, acetonitrile, or a mixed solvent thereof. Preferably, the reaction solvent is N,N-dimethylformamide, N-methylpyrrolidone, dimethyl sulfoxide, methanol, ethanol, isopropanol, or acetonitrile, further preferably N,N-dimethylformamide, or ethanol. The reaction temperature may be selected from a range of from 20 to 120° C., preferably from 60 to 70° C., or from 70 to 80° C.

According to the technical solutions described in the above schemes, optionally, when R1 is selected from hydroxymethyl, 2-(trimethylsilyl)ethoxymethyl (SEM), benzyloxymethyl (Bom), or methoxymethyl, and R2 is a diamide protecting group, the synthesis of compound I from compound 4P2 can adopt the two-step removal method as mentioned above.

It should be noted that each step of the method of the present invention can be carried out continuously without purification. For example, in the following schemes: compound 2 is cyclized with a hydrazine compound to prepare compound 3, which is subjected to amino protection to prepare compound 3P, which reacts with compound SM2 to prepare compound 4P1, which is subjected to transformation of the R4 functional group to prepare compound 4P2, from which compound I is obtained. "The process of obtaining compound 3 from compound 2, and then subjecting compound 3 to amino protection to prepare compound 3P" can be the one that after obtaining compound 3 from compound 2, subjecting compound 3 without purification to amino protection to prepare compound 3P. Other steps or processes can also be performed similarly. The embodiments of carrying out the method of the present invention in this way are also within the scope of the present invention.

The present invention also relates to intermediates obtained during the preparation process, for example, the intermediate compounds 5 and 6 having the following formulas

5

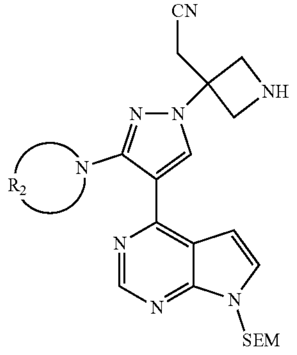

-continued

6

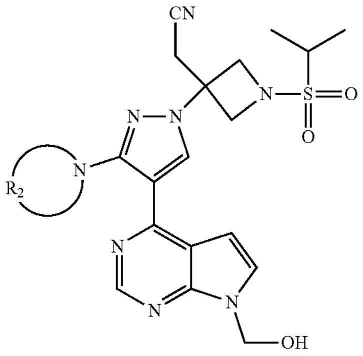

wherein, R2 is hydrogen or an amino protecting group, and SEM refers to 2-(trimethylsilyl)ethoxymethyl.

Specifically, they are selected from the group consisting of the following compounds 5a, 5b, 5c and compounds 6a, 6b, 6c:

5a

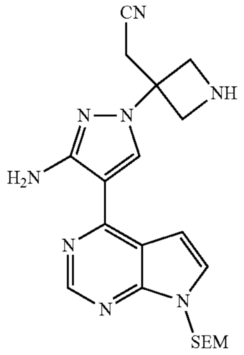

5b

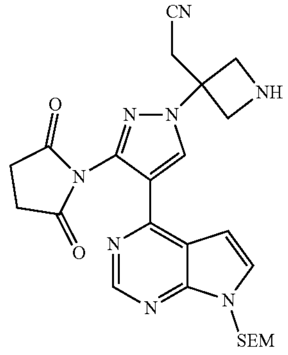

5c

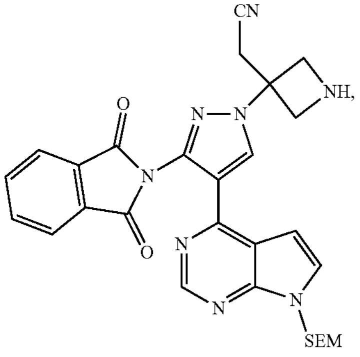

-continued
6a
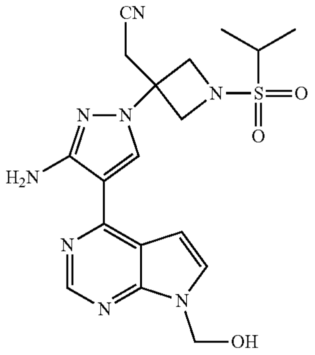
6b
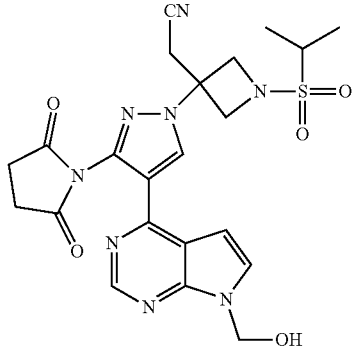
6c
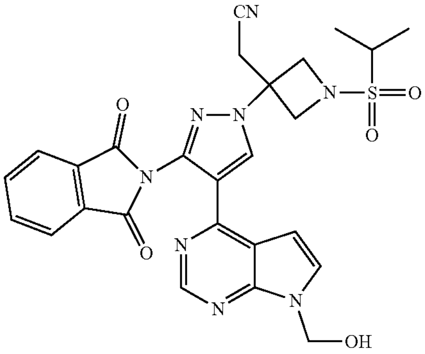
wherein SEM refers to 2-(trimethylsilyl)ethoxymethyl.
The invention also relates to intermediates obtained during the preparation process, for example,
3
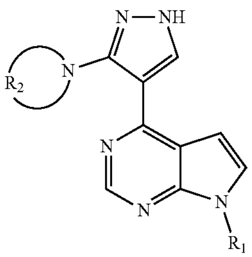
-continued
3a
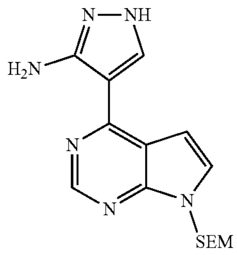
3b
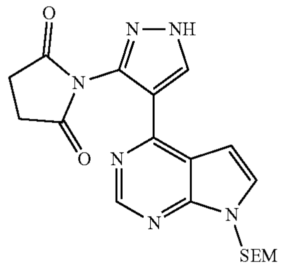
3c
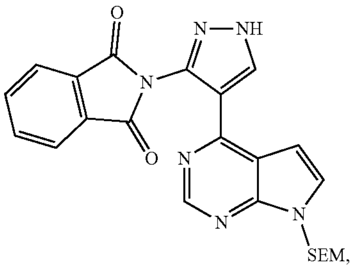
4a
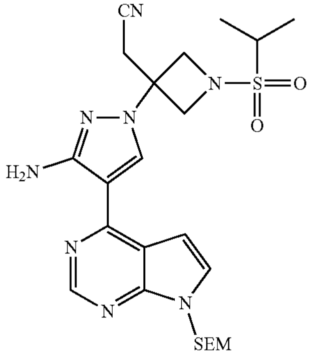
4b
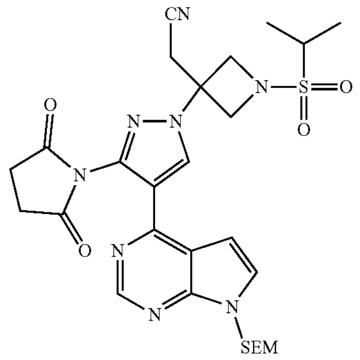

-continued

4c

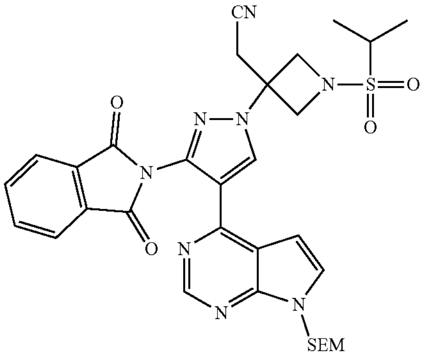

4P1

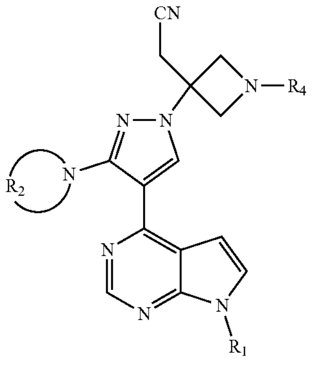

4d

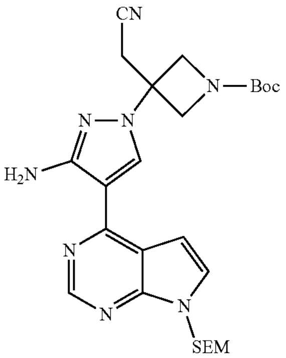

4e

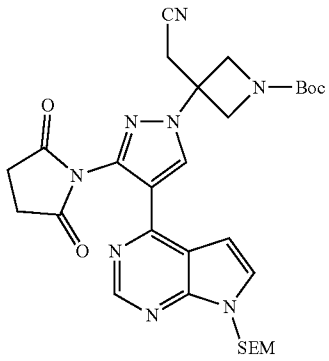

-continued

4f

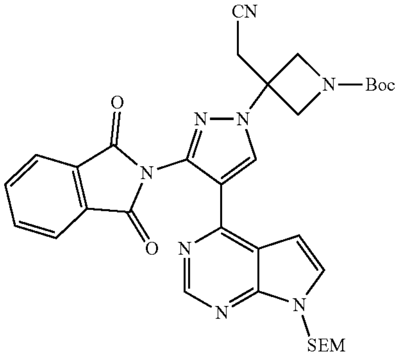

wherein, R1 and R2 are hydrogen or an amino protecting group, R4 is hydrogen, an amino protecting group or isopropylsulfonyl, SEM refers to 2-(trimethylsilyl) ethoxymethyl; and Boc refers to tert-butoxycarbonyl.

In order to better illustrate the implementation of the present application, relevant information and terms are described and defined in the description and some embodiments of the present application.

In the present application, the compound numbering follows the principles:

(1) Arabic numeral refers to a class of compounds with a substituent defined by a specific structure, such as:

3

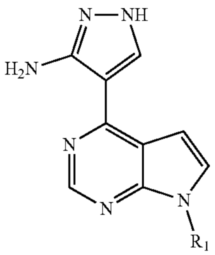

(2) The combination of Arabic numeral and a lowercase letter refers to a specific compound having a specific structure, such as:

3a

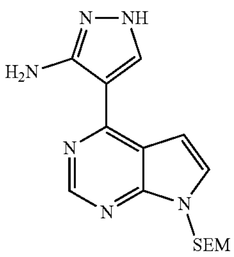

(3) The combination of Arabic numeral and capital letter P specifically refers to the compound whose 3-position amino group is protected (R2 is an amino protecting group other than hydrogen), such as:

3P

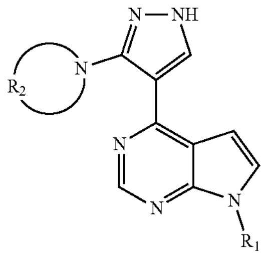

4P2

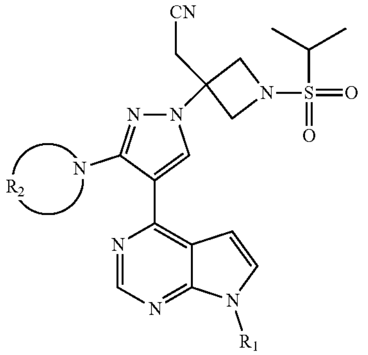

In the present application, “SEM-” refers to 2-(trimethylsilyl)ethoxymethyl.

In the present application, “DBU” refers to 1,8-diazabicyclo[5.4.0]undec-7-ene.

In the present application, “DMF-DMA” refers to N,N-dimethylformamide dimethyl acetal.

In the present application, “hydrazine compound” includes an aqueous solution and an organic solution of hydrazine, and a salt compound of hydrazine.

In the present application, “3-position amino group” refers to the functional group and the position as shown by in the following formula:

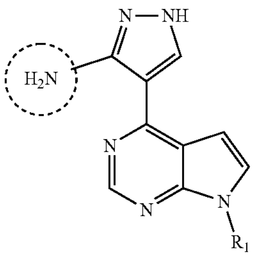

In the present application, the chemical bond represented by “ ” means that the direction of the chemical bond attaching to the alkene group is not limited. For example, compound 2 may comprise the following two configurations.

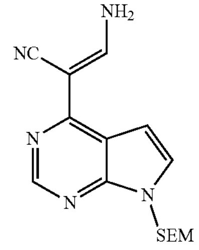

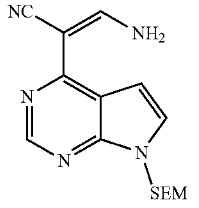

In the present application, said amino protecting groups or cyclic imide protecting groups and their attachment or removal methods can be achieved by conventional methods in the art, which methods can be completed by one- or more-step reactions.

In the present application, said reactions may optionally be carried out in a solvent. All solvents used in the present application are commercially available and can be used without purification.

The preparation method of the present application has the advantages of simple operation, mild reaction conditions and high yield, avoids the problems of low yield, a large amount of impurities and difficult separation of the same in original routes, reduces production cost, and is suitable for industrial production.

The following examples are provided as further detailed non-limiting illustrations of the technical solutions of the present invention, which should not be construed as limiting the scope of the present invention, but as merely illustrations and typical representatives of the present invention.

Example 1

Preparation of 2-{3-[3-amino-4-(7H-pyrrolo[2,3-d]pyrimidin-4-yl)-1H-pyrazol-1-yl]-1-(isopropylsulfonyl)azetidin-3-yl}acetonitrile (I)

Step A: 4-(7-{[2-(trimethylsilyl)ethoxy]methyl}-7H-pyrrolo[2,3-d]pyrimidin-4-yl)-1H-pyrazole-3-amine

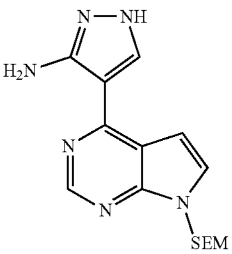 [SMILES: C[Si](C)(C)CCOCn1ccc2c(-c3c[nH]nc3N)ncnc21]

To a 10 L reaction flask 5.0 L of N,N-dimethylformamide and 805 g of 3-amino-2-(7-{[2-(trimethylsilyl)ethoxy]methyl}-7H-pyrrolo[2,3-d]pyrimidin-4-yl)acrylonitrile (2.55 mol, 1.0 eq) were added under stirring at room temperature, and stirred to be dissolved, and then 800 g of hydrazine hydrate (12.78 mol, 5.0 eq) and 150 g of DMF-DMA (1.26 mol, 0.5 eq) were added sequentially. After the addition was completed, the temperature was raised to 90-100° C. for 6 hours, then the reaction was stopped, and lowered to room temperature. The reaction solution was transferred into a 20 L transfer barrel, added with 10.0 L of water, stirred, solid precipitated, centrifuged and filtered, and the filter cake was dried at 55° C. The weight was 660 g and the yield was 78.3%.

$^1$H-NMR (400 MHz, DMSO-d6): δ 12.01 (s, 1H), 8.65 (s, 1H), 8.24 (s, 1H), 7.62 (d, 1H, J=3.2 Hz), 7.02 (d, 1H, J=3.5 Hz), 6.57 (s, 2H), 5.60 (s, 2H), 3.54-3.51 (m, 2H, J=8.0 Hz), 0.85-0.81 (m, 2H, J=8.0 Hz), −0.09 (s, 9H); HRMS (ESI) calcd. for C15H22N6OSi $[M+H]^+$ 330.1624; Found: m/z=331.1661[M+H]+.

Step B: 1-[4-(7-{[2-(trimethylsilyl)ethoxy]methyl}-7H-pyrrolo[2,3-d]pyrimidin-4-yl)-1H-pyrazol-3-yl] pyrrolidine-2,5-dione

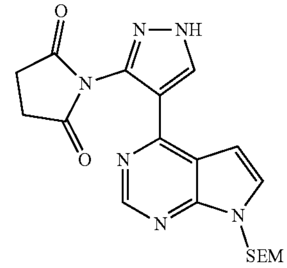 [SMILES: C[Si](C)(C)CCOCn1ccc2c(-c3c[nH]nc3N3C(=O)CCC3=O)ncnc21]

To a 3 L reaction flask 1.2 L of toluene, 165 g of 4-(7-{[2-(trimethylsilyl)ethoxy]methyl}-7H-pyrrolo[2,3-d] pyrimidin-4-yl)-1H-pyrazole-3-amine (0.50 mol, 1.0 eq), and 55.0 g of succinic anhydride (0.55 mol, 1.1 eq) were added under stirring at room temperature.

A water separator was installed. The reaction system was heated to reflux, and reacted while separating the water until the raw materials were converted completely. Then the reaction was stopped, and lowered the temperature. To the reaction system 600 mL of isopropyl ether was added, stirred and crystallized, and filtered. The resulting solid was dried to constant weight. The weight was 176 g and the yield was 85.4%.

$^1$H-NMR (400 MHz, $CDCl_3$): δ 12.03 (s, 1H), 8.71 (s, 1H), 8.27 (s, 1H), 7.25 (d, 2H, J=4.0 Hz), 6.55 (s, 2H, J=4.0 Hz), 5.58 (s, 2H), 3.50 (m, 2H, J=8.0 Hz), 2.97 (m, 4H), 0.92-0.88 (m, 2H, J=8.0 Hz), −0.06 (s, 9H).

Step C: tert-butyl 3-(cyanomethyl)-3-(3-(2,5-dioxopyrrolidin-1-yl)-4-(7-((2-(trimethylsilyl)ethoxy) methyl)-7H-pyrrolo[2,3-d]pyrimidin-4-yl)-1H-pyrazol-1-yl)azetidinyl-1-carboxylate

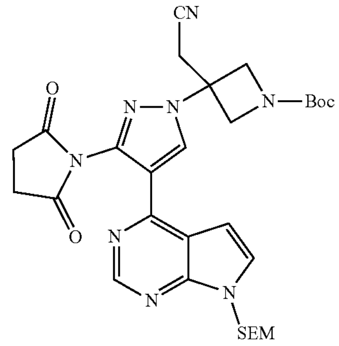 [SMILES: CC(C)(C)OC(=O)N1CC(CC#N)(n2cc(-c3ncnc4c3ccn4COCC[Si](C)(C)C)c(N3C(=O)CCC3=O)n2)C1]

To a 3 L reaction flask 124 g of 1-[4-(7-{[2-(trimethylsilyl)ethoxy]methyl}-7H-pyrrolo[2,3-d]pyrimidin-4-yl)-1H-pyrazol-3-yl]pyrrolidine-2,5-dione (0.30 mol, 1.0 eq), 91.5 g of DBU (0.60 mol, 2.0 eq), 1.8 L of acetonitrile, and 64.0 g of tert-butyl 3-(cyanomethylene)azetidinyl-1-carboxylate (0.32 mol, 1.1 eq) were added, heated to 30-40° C., stirred to react for 5 h. Then the reaction was stopped, and the reaction solution was concentrated to recover acetonitrile. The residue was added with 600 mL of isopropanol, stirred and crystallized, and filtered. The resulting solid was dried to obtain an off-white solid. The weight was 170 g and the yield was 93.4%.

$^1$H-NMR (400 MHz, $CDCl_3$): δ8.75 (s, 1H), 8.55 (s, 1H), 7.46 (d, 1H, J=4.0 Hz), 6.74 (d, 1H, J=4.0 Hz), 5.66 (s, 2H), 4.70 (m, 2H, J=8.0 Hz), 4.32 (m, 2H, J=8.0 Hz), 3.50-3.55 (m, 2H, J=8.0 Hz), 3.43 (s, 2H), 2.96 (s, 4H), 1.40 (s, 9H), 0.91-0.89 (m, 2H, J=8.0 Hz), −0.06 (s, 9H).

Step D: 2-{3-[3-(2,5-dioxopyrrolidin-1-yl)-4-(7-{[-(trimethylsilyl)ethoxy]methyl}-7H-pyrrolo[2,3-d] pyrimidin-4-yl)-1H-pyrazol-1-yl]azetidin-3-yl}acetonitrile hydrochloride

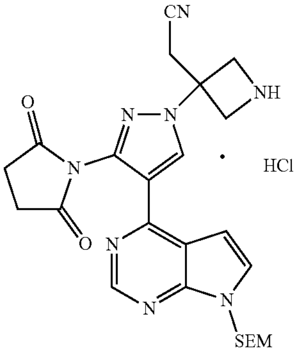 [SMILES: C[Si](C)(C)CCOCn1ccc2c(-c3cn(C4(CC#N)CNC4)nc3N3C(=O)CCC3=O)ncnc21 ; Cl]

To a 3 L reaction flask 160 g of tert-butyl 3-(cyanomethyl)-3-[3-(2,5-dioxopyrrolidin-1-yl)-4-(7-{[2-(trimethylsilyl)ethoxy]methyl}-7H-pyrrolo[2,3-d]pyrimidin-4-yl)-1H-pyrazol-1-yl]azetidinyl-1-carboxylate (0.26 mol, 1.0 eq) and 1.6 L of dichloromethane were added under the conditions of stirring at room temperature, and stirred to be dissolved. With controlling the temperature at 10-20° C., 330 ml of a solution of hydrogen chloride in tetrahydrofuran (4 mol/L, 1.32 mol, 5.0 eq) was added. The reaction was stirred, and filtered. The filter cake was dried, and weighed 136 g, and the yield was 95.1%.

$^1$H-NMR (400 MHz, $CDCl_3$): δ8.69 (s, 1H), 8.43 (s, 1H), 7.35 (d, 1H, J=4.0 Hz), 6.69 (d, 1H, J=4.0 Hz), 5.60 (s, 2H), 4.33 (d, 2H, J=8.0 Hz), 3.92 (d, 2H, J=8.0 Hz), 3.49 (m, 2H, J=8.0 Hz), 3.41 (s, 2H), 2.93 (s, 4H), 1.35 (m, 1H), −0.08 (s, 9H).

Step E: 2-{3-[3-(2,5-dioxopyrrolidin-1-yl)-4-(7-{[2-(trimethylsilyl)ethoxy]methyl}-7H-pyrrolo[2,3-d]pyrimidin-4-yl)-1H-pyrazol-1-yl]-1-(isopropylsulfonyl)azetidin-3-yl}acetonitrile

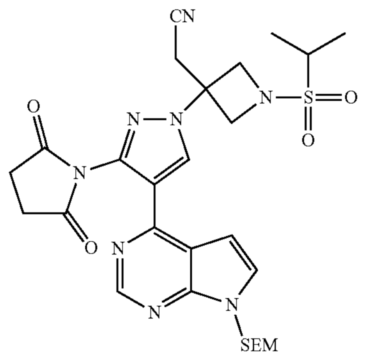 [SMILES: CC(C)S(=O)(=O)N1CC(CC#N)(n2cc(-c3ncnc4c3ccn4COCC[Si](C)(C)C)c(N3C(=O)CCC3=O)n2)C1]

To a 2 L reaction flask 120 g of 2-{3-[3-(2,5-dioxopyrrolidin-1-yl)-4-(7-{[-(trimethylsilyl)ethoxy]methyl}-7H-pyrrolo[2,3-d]pyrimidin-4-yl)-1H-pyrazol-1-yl]azetidin-3-yl}acetonitrile hydrochloride (0.22 mol, 1.0 eq) and 600 ml of dichloromethane were added under the conditions of stirring at room temperature. With controlling the temperature at 0-5° C., 68.0 g of triethylamine (0.66 mol, 3.0 eq) was slowly added dropwise under stirring. After the addition was completed, the reaction was stirred for another 30 min with controlling the temperature. 40.0 g of isopropylsulfonyl chloride (0.28 mol, 1.3 eq) was slowly added dropwise. After the addition was completed, the reaction was stirred for another 1 h, and then stopped. The reaction solution was quenched with addition of water, and concentrated to recover dichloromethane. The resulting residue was washed sequentially with 300 mL of water and 300 mL of ethanol/water (volume ratio of 1:1) mixture, and filtered to obtain an off-white solid, which was dried with air blast at 55° C. to constant weight. The weight was 118 g and the yield was 87.4%.

$^{1}$H-NMR (500 MHz, DMSO-d6): δ 9.07 (s, 1H), 8.74 (s, 1H), 7.86 (d, 1H, J=3.5 Hz), 7.18 (d, 1H, J=3.5 Hz), 5.64 (s, 2H), 4.62-4.61 (d, 2H, J=9.0 Hz), 4.24-4.22 (d, 2H, J=9.0 Hz), 3.75 (s, 2H), 3.54-3.51 (m, 2H, J=8.0 Hz), 3.37 (m, 1H, J=7.0 Hz), 2.92 (m, 4H), 1.29-1.27 (d, 6H, J=6.5 Hz), 0.84-0.81 (t, 2H, J=8.0 Hz), −0.08~−0.10 (s, 9H). HRMS (ESI) calcd. for C27H36N8O5SSi, $[M+H]^+$ 612.7810; Found: m/z=613.2313$[M+1]^+$; m/z=635.2134 $[M+Na]^+$.

Step F: 2-(3-{3-(2,5-dioxopyrrolidin-1-yl)-4-[7-(hydroxymethyl)-7H-pyrrolo[2,3-d]pyrimidin-4-yl]-1H-pyrazol-1-yl}-1-(isopropylsulfonyl)azetidin-3-yl)acetonitrile

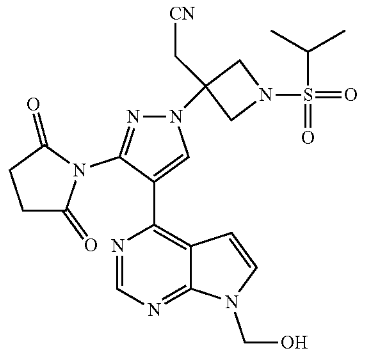 [SMILES: CC(C)S(=O)(=O)N1CC(CC#N)(n2cc(-c3ncnc4c3ccn4CO)c(N3C(=O)CCC3=O)n2)C1]

To a 2 L reaction flask, under stirring at room temperature, 92.0 g of 2-{3-[3-(2,5-dioxopyrrolidin-1-yl)-4-(7-{[2-(trimethylsilyl)ethoxy]methyl}-7H-pyrrolo[2,3-d]pyrimidin-4-yl)-1H-pyrazol-1-yl]-1-(isopropylsulfonyl)azetidin-3-yl}acetonitrile (0.15 mol, 1.0 eq) and 500 mL of acetonitrile were added, and 43.0 g of boron trifluoride diethyl etherate (0.30 mol, 2.0 eq) was slowly added dropwise by using a pressure equalizing funnel. After the addition was completed, with the temperature raising to 40-50° C., the reaction was stirred for 5 h. Then the reaction was stopped, cooled to room temperature, added with a saturated sodium carbonate solution to adjust the pH to 9-10, solid precipitated, and filtered. The filter cake was washed with addition of 500 mL of water, and dried to obtain 70.4 g of off-white solid with a yield of 91.4%.

$^{1}$H-NMR: (500 MHz, DMSO-d6): δ ppm 9.04 (s, 1H), 8.73 (s, 1H), 7.78-7.78 (d, 1H, J=3.5 Hz), 7.12-7.13 (d, 1H, J=3.5 Hz), 6.72 (s, 1H), 5.62 (s, 2H), 4.60-4.62 (d, 2H, J=9.5 Hz), 4.22-4.24 (d, 2H, J=9.0 Hz), 3.75 (s, 2H), 3.35-3.38 (m, 1H, J=6.5 Hz), 2.92 (m, 4H), 1.18-1.29 (m, 6H, J=7.0 Hz). HRMS (ESI) calcd. for C22H24N8O5S, [M+H]+ 513.5450; Found: m/z=513.1632[M+1]+; m/z=535.1455[M+Na]+.

Step G: 2-{3-[3-amino-4-(7H-pyrrolo[2,3-d]pyrimidin-4-yl)-1H-pyrazol-1-yl]-1-(isopropylsulfonyl)azetidin-3-yl}acetonitrile

I

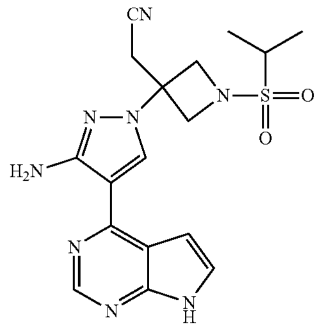

To a 1 L reaction flask 62.0 g of 2-(3-{3-(2,5-dioxopyrrolidin-1-yl)-4-[7-(hydroxymethyl)-7H-pyrrolo[2,3-d]pyrimidin-4-yl]-1H-pyrazol-1-yl}-1-(isopropylsulfonyl)azetidin-3-yl)acetonitrile (0.12 mol, 1.0 eq) was added, and then 600 mL of ethanol and 38.0 g of hydrazine hydrate (0.60 mol, 5.0 eq) were added, under stirring at room temperature. The reaction system was heated up to reflux for 3 h. Then the reaction was stopped, and cooled to room temperature. The reaction solution was poured into 1.2 L of ice water, stirred and crystallized, and filtered. The filter cake was washed with water to obtain a light yellow solid. The resulting solid was dried with air blast at 60° C. to constant weight. The weight was 44.7 g, and the yield was 92.4%.

$^{1}$H NMR (500 MHz, DMSO-d6): δ 12.05 (s, 1H), 8.67 (s, 1H), 8.61 (s, 1H), 7.57 (d, 1H, J=4.0 Hz), 7.10 (d, 1H, J=4.0 Hz), 6.41 (s, 2H), 4.57 (d, 2H, J=8.5 Hz), 4.11 (d, 2H, J=8.7 Hz), 3.60 (s, 2H), 3.38-3.33 (m, 1H), 1.28-1.26 (m, 6H); HRMS (ESI) calcd. for C17H20N8O2S [M+H]+ 400.1430; Found: m/z=401.1509 [M+H]+.

Example 2

Preparation of 2-{3-[3-amino-4-(7H-pyrrolo[2,3-d]pyrimidin-4-yl)-1H-pyrazol-1-yl]-1-(isopropylsulfonyl)azetidin-3-yl}acetonitrile (I)

Step A: 4-(7-{[2-(trimethylsilyl)ethoxy]methyl}-7H-pyrrolo[2,3-d]pyrimidin-4-yl)-1H-pyrazole-3-amine

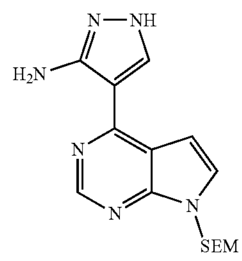 [SMILES: C[Si](C)(C)CCOCn1ccc2c(-c3c[nH]nc3N)ncnc21]

To a 3 L reaction flask 315 g of 3-amino-2-(7-{[2-(trimethylsilyl)ethoxy]methyl}-7H-pyrrolo[2,3-d]pyrimidin-4-yl)acrylonitrile (1.0 mol, 1.0 eq) and 1.5 L of isopropanol were added under stirring at room temperature, stirred for 10 min to mix well, and then 190 g of hydrazine hydrate (3.04 mol, 3.0 eq) and 96.0 g of DMF-DMA (0.80 mol, 0.8 eq) were added.

After the addition was completed, the reaction was heated to reflux for 6 hours. The reaction was stopped, and lowered to room temperature. The reaction solution was transferred into a 10 L transfer barrel, added with 5.0 L of water, stirred, solid precipitated, centrifuged and filtered, and dried. The weight was 283 g, and the yield was 85.8%.

Step B: 2-[4-(7-{[2-(trimethylsilyl)ethoxy]methyl}-7H-pyrrolo[2,3-d]pyrimidin-4-yl)-1H-pyrazol-3-yl]isoindolinyl-1,3-dione

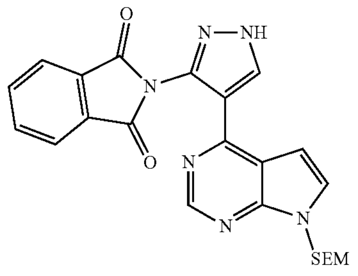 [SMILES: C[Si](C)(C)CCOCn1ccc2c(-c3c[nH]nc3N3C(=O)c4ccccc4C3=O)ncnc21]

To a 3 L reaction flask 1.2 L of toluene, 165 g of 4-(7-{[2-(trimethylsilyl)ethoxy]methyl}-7H-pyrrolo[2,3-d]pyrimidin-4-yl)-1H-pyrazole-3-amine (0.50 mol, 1.0 eq), and 74.0 g of phthalic anhydride (0.50 mol, 1.0 eq) were added under stirring at room temperature. A water separator was installed. The reaction system was heated to reflux, and reacted while separating the water until the raw materials were converted completely, stopped the heating, continued stirring to room temperature, and filtered. The resulting solid was dried to constant weight. The weight was 185 g and the yield was 80.4%.

$^1$H-NMR (400 MHz, DMSO-d6): δ 13.81 (s, 1H), 8.93 (s, 1H), 8.18 (s, 1H), 7.98-7.91 (m, 4H, J=4.0 Hz), 7.75-7.74 (d, 2H, J=4.0 Hz), 5.55 (s, 2H), 3.47-3.43 (m, 2H, J=8.0 Hz), 0.78-0.74 (m, 2H, J=8.0 Hz), −0.16 (s, 9H).

Step C: tert-butyl 3-(cyanomethyl)-3-[3-(1,3-dioxoisoindolin-2-yl)-4-(7-{[2-(trimethylsilyl)ethoxy]methyl}-7H-pyrrolo[2,3-d]pyrimidin-4-yl)-1H-pyrazol-1-yl]azetidinyl-1-carboxylate

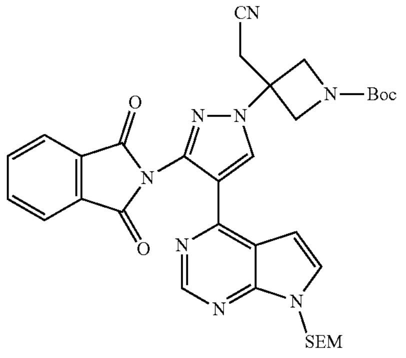 [SMILES: CC(C)(C)OC(=O)N1CC(CC#N)(n2cc(-c3ncnc4c3ccn4COCC[Si](C)(C)C)c(N3C(=O)c4ccccc4C3=O)n2)C1]

To a 3 L reaction flask 93.0 g of 2-[4-(7-{[2-(trimethylsilyl)ethoxy]methyl}-7H-pyrrolo[2,3-d]pyrimidin-4-yl)-1H-pyrazol-3-yl]isoindolinyl-1,3-dione (0.20 mol, 1.0 eq), 91.5 g of DBU (0.60 mol, 3.0 eq), 1.2 L of acetonitrile, and 44.0 g of tert-butyl 3-(cyanomethylene)azetidinyl-1-carboxylate (0.22 mol, 1.1 eq) were added under stirring at room temperature. With the temperature rising to 30-40° C., the reaction was stirred for 5 h and then stopped. The reaction solution was concentrated, and the residue was added with 500 mL of isopropanol, stirred and crystallized, and filtered, and the solid was dried to obtain an off-white solid. The weight was 123 g and the yield was 93.2%.

$^1$H-NMR (400 MHz, $CDCl_3$): δ8.49 (s, 1H), 8.45 (s, 1H), 7.96-7.94 (m, 2H, J=4.0 Hz), 7.82-7.80 (m, 2H, J=4.0 Hz), 7.36-7.35 (d, 2H, J=4.0 Hz), 6.66-6.65 (d, 2H, J=4.0 Hz), 5.60 (s, 2H), 4.65-4.63 (d, 2H, J=8.0 Hz), 4.35-4.32 (m, 2H, J=8.0 Hz), 3.50-3.46 (m, 2H, J=8.0 Hz), 3.35 (s, 2H), 1.47 (s, 9H), 0.90-0.86 (m, 2H, J=8.0 Hz), −0.08 (s, 9H).

Step D: 2-{3-[3-(1,3-dioxoisoindolin-2-yl)-4-(7-{[2-(trimethylsilyl)ethoxy]methyl}-7H-pyrrolo[2,3-d]pyrimidin-4-yl)-1H-pyrazol-1-yl]-1-(isopropylsulfonyl)azetidin-3-yl}acetonitrile

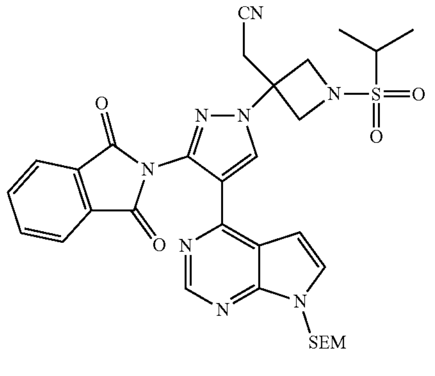 [SMILES: CC(C)S(=O)(=O)N1CC(CC#N)(n2cc(-c3ncnc4c3ccn4COCC[Si](C)(C)C)c(N3C(=O)c4ccccc4C3=O)n2)C1]

To a 2 L reaction flask 92.0 g of tert-butyl 3-(cyanomethyl)-3-[3-(1,3-dioxoisoindolin-2-yl)-4-(7-{[2-(trimethylsilyl)ethoxy]methyl}-7H-pyrrolo[2,3-d]pyrimidin-4-yl)-1H-pyrazol-1-yl]azetidinyl-1-carboxylate (0.14 mol, 1.0 eq) and LOL of ethyl acetate were added under stirring at room temperature, and stirred to be dissolved. With the temperature control at 20-25° C., 175 mL of a solution of hydrogen chloride in tetrahydrofuran (4 mol/L, 0.70 mol, 5.0 eq) was added, stirred and reacted, and the solids were gradually precipitated out in the reaction solution. After the reaction was completed, the solution was filtered, and the solid was transferred to a 1.0 L three-necked flask, to which 600 mL of dichloromethane and 43.0 g of triethylamine (0.42 mol, 3.0 eq) were added, stirred, cooled down to 0-5° C., and slowly added with 24.0 g of isopropylsulfonyl chloride (0.17 mol, 1.2 eq). After the addition is completed, the reaction solution was stirred for another 30 min. Then the reaction was stopped, and quenched with addition of water. The organic phase was washed with purified water twice, 200 mL for each time. The liquids were separated, and the organic phase was dried with addition of anhydrous sodium sulfate for 1 h, and filtered to remove the drying agent. The organic phase was concentrated under reduced pressure to obtain 67.5 g of light yellow solid with a yield of 73.0%.

$^1$H-NMR (400 MHz, $CDCl_3$): δ 9.13 (s, 1H), 8.26 (s, 1H), 8.02-7.97 (m, 4H), 7.88-7.87 (d, 1H, J=4.0 Hz), 7.20-7.19 (d, 1H, J=4.0 Hz), 5.60 (s, 2H), 4.68-4.66 (d, 2H, J=8.0 Hz), 4.28-4.26 (d, 2H, J=8.0 Hz), 3.79 (s, 2H), 3.51-3.47 (m, 2H, J=8.0 Hz), 3.42-3.37 (m, 1H, J=8.0 Hz), 1.30-1.28 (d, 2H, J=8.0 Hz), 0.82-0.78 (m, 1H, J=8.0 Hz), −0.08 (s, 9H).

Step E: 2-(3-{3-(1,3-dioxoisoindolin-2-yl)-4-[7-(hydroxymethyl)-7H-pyrrolo[2,3-d]pyrimidin-4-yl]-1H-pyrazol-1-yl}-1-(isopropylsulfonyl)azetidin-3-yl) acetonitrile

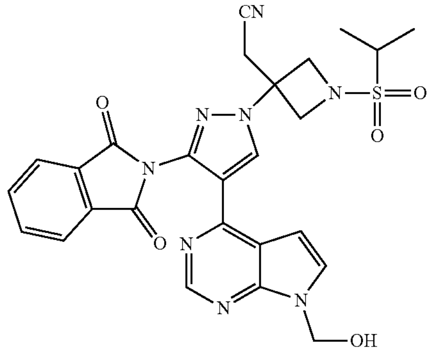 [SMILES: CC(C)S(=O)(=O)N1CC(CC#N)(n2cc(-c3ncnc4c3ccn4CO)c(N3C(=O)c4ccccc4C3=O)n2)C1]

To a 1 L reaction flask, under stirring at room temperature, 66.0 g of 2-{3-[3-(1,3-dioxoisoindolin-2-yl)-4-(7-{[2-(trimethylsilyl)ethoxy]methyl}-7H-pyrrolo[2,3-d]pyrimidin-4-yl)-1H-pyrazol-1-yl]-1-(isopropylsulfonyl)azetidin-3-yl}acetonitrile (0.10 mol, 1.0 eq) and 500 mL of acetonitrile were added, and 34.0 g of boron trifluoride diethyl etherate (0.15 mol, 1.5 eq) was slowly added dropwise by using a pressure equalizing funnel. After the addition was completed, the reaction was stirred at room temperature for 2 h, and then stopped. The reaction solution was concentrated under reduced pressure, and the residue was added with a saturated sodium carbonate solution to adjust the pH to 9-10, and extracted with 2×300 mL of ethyl acetate. The organic phases were combined, and washed once with 200 mL of water. The liquids were separated, and the organic phase was dried, evaporated to dryness, and dried to obtain 48.5 g of off-white solid with a yield of 86.6%.

Step F: 2-{3-[3-amino-4-(7H-pyrrolo[2,3-d]pyrimidin-4-yl)-1H-pyrazol-1-yl]-1-(isopropylsulfonyl) azetidin-3-yl}acetonitrile

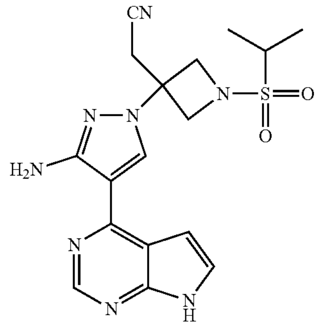

I

To a 1 L reaction flask, under stirring at room temperature, 45.0 g of 2-(3-{3-(1,3-dioxoisoindolin-2-yl)-4-[7-(hydroxymethyl)-7H-pyrrolo[2,3-d]pyrimidin-4-yl]-1H-pyrazol-1-yl}-1-(isopropylsulfonyl)azetidin-3-yl)acetonitrile (0.08 mol, 1.0 eq), 360 mL of ethanol, and 225 g of ammonia water (with a content of 25% to 28%, 1.6 mol, 20.0 eq) were added and stirred at room temperature for 12 h. The reaction was stopped, and the reaction system was poured into 500 mL of ice water, stirred and crystallized, and filtered. The filter cake was dried to obtain a solid. The weight was 29.3 g, and the yield was 91.3%.

Example 3

Preparation of 2-{3-[3-amino-4-(7H-pyrrolo[2,3-d]pyrimidin-4-yl)-1H-pyrazol-1-yl]-1-(isopropylsulfonyl)azetidin-3-yl}acetonitrile (I)

Step A: 4-(7-{[2-(trimethylsilyl)ethoxy]methyl}-7H-pyrrolo[2,3-d]pyrimidin-4-yl)-1H-pyrazole-3-amine

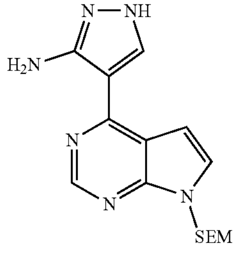 [SMILES: C[Si](C)(C)CCOCn1ccc2c(-c3c[nH]nc3N)ncnc21]

To a 1 L reaction flask 500 mL of n-butanol, and 80.0 g of 3-amino-2-(7-{[2-(trimethylsilyl)ethoxy]methyl}-7H-pyrrolo[2,3-d]pyrimidin-4-yl)acrylonitrile (0.25 mol, 1.0 eq) were added under stirring at room temperature, stirred to mix well, and then 47.0 g of hydrazine hydrate (0.75 mol, 3.0 eq) and 55.0 g of N,N-dimethylformamide diethyl acetal (038 mol, 1.5 eq) were added. The reaction was heated to reflux for 6 h, and then stopped, and cooled to room temperature. The reaction solution was concentrated under reduced pressure to recover n-butanol, and the residue was added with 400 mL of water, stirred and washed, and filtered. The resulting filter cake was dried to constant weight. The weight was 68.8 g, and the yield was 82.1%.

Step B: tert-butyl 3-[3-amino-4-(7-{[2-(trimethylsilyl)ethoxy]methyl}-7H-pyrrolo[2,3-d]pyrimidin-4-yl)-1H-pyrazol-1-yl]-3-(cyanomethyl)azetidinyl-1-carboxylate

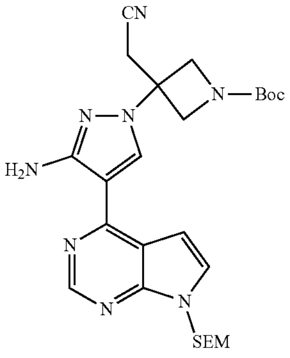 [SMILES: CC(C)(C)OC(=O)N1CC(CC#N)(n2cc(-c3ncnc4c3ccn4COCC[Si](C)(C)C)c(N)n2)C1]

To a 1 L reaction flask 300 mL of N,N-dimethylformamide, 60.0 g of 4-(7-{[2-(trimethylsilyl)ethoxy]methyl}-7H-pyrrolo[2,3-d]pyrimidin-4-yl)-1H-pyrazole-3-amine (0.18 mol, 1.0 eq), 42.0 g of tetramethylguanidine (0.36 mol, 2.0 eq) and 42.0 g of tert-butyl 3-(cyanomethylene)azetidinyl-1-carboxylate (0.22 mol, 1.2 eq) were added under stirring at room temperature. After the addition is completed, with controlling the temperature at 45° C., the mixture reacts for 24 hours, and then the reaction was stopped. The reaction solution was quenched with addition of water, and extracted with addition of ethyl acetate (300 mL*2). The organic phase was washed with water (200 mL*2), and dried. The organic phase was evaporated to dryness, and the residue was added with 300 mL of isopropanol, stirred and crystallized, and filtered to obtain a solid. The resulting solid was dried at 55° C. to constant weight. The weight was 83.8 g and the yield was 87.9%.

$^1$H NMR (400 MHz, CDCl3): δ 8.78 (s, 1H), 8.06 (s, 1H), 7.34 (d, 1H), 6.67 (d, 1H), 5.74 (s, 2H), 5.64 (s, 2H), 4.47 (d, 2H, J=8.5 Hz), 4.20 (d, 2H, J=8.7 Hz), 3.53-3.49 (m, 2H), 3.24 (s, 2H), 1.44 (s, 1H), 0.91-0.87 (m, 2H), −0.08 (s, 9H).

Step C: tert-butyl 3-(cyanomethyl)-3-[3-(1,3-dioxoisoindolin-2-yl)-4-(7-{[2-(trimethylsilyl)ethoxy]methyl}-7H-pyrrolo[2,3-d]pyrimidin-4-yl)-1H-pyrazol-1-yl]azetidinyl-1-carboxylate

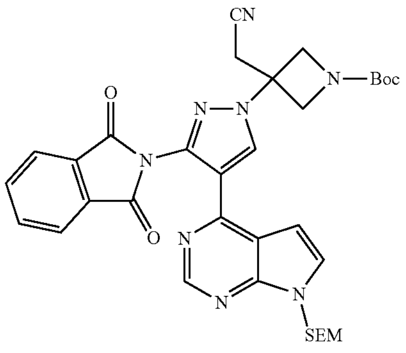 [SMILES: CC(C)(C)OC(=O)N1CC(CC#N)(n2cc(-c3ncnc4c3ccn4COCC[Si](C)(C)C)c(N3C(=O)c4ccccc4C3=O)n2)C1]

To a 2 L reaction flask 78.6 g of tert-butyl 3-[3-amino-4-(7-{[2-(trimethylsilyl)ethoxy]methyl}-7H-pyrrolo[2,3-d]pyrimidin-4-yl)-1H-pyrazol-1-yl]-3-(cyanomethyl)azetidinyl-1-carboxylate (0.15 mol, 1.0 eq), 550 mL of toluene, and 24.5 g of phthalic anhydride (0.16 mol, 1.1 eq) were added under stirring at room temperature. A water separator was installed. The reaction system was heated to reflux, and reacted for 6 h while separating the water, stopped the heating, and lowered the temperature. To the reaction system 600 mL of n-hexane was added, stirred and crystallized, and filtered. The filter cake was added with 300 mL of isopropyl ether, stirred and washed, and filtered. The resulting solid was dried. The weight was 84.3 g and the yield was 86.0%.

$^1$H-NMR (400 MHz, $CDCl_3$): δ 8.49 (s, 1H), 8.45 (s, 1H), 7.96-7.94 (m, 2H, J=2.7 Hz), 7.82-7.80 (m, 2H, J=2.7 Hz), 7.36 (d, 1H, J=4.0 Hz), 6.66 (d, 1H, J=4.0 Hz), 5.60 (s, 2H), 4.65 (d, 1H, J=8.0 Hz), 4.35 (d, 1H, J=8.0 Hz), 3.50-3.46 (m, 2H, J=8.0 Hz), 3.35 (s, 2H), 1.47 (s, 9H), 0.90-0.86 (m, 2H, J=8.0 Hz), −0.08 (s, 9H).

Step D: 2-{3-[3-(1,3-dioxoisoindolin-2-yl)-4-(7-{[2-(trimethylsilyl)ethoxy]methyl}-7H-pyrrolo[2,3-d]pyrimidin-4-yl)-1H-pyrazol-1-yl]-1-(isopropylsulfonyl)azetidin-3-yl}acetonitrile

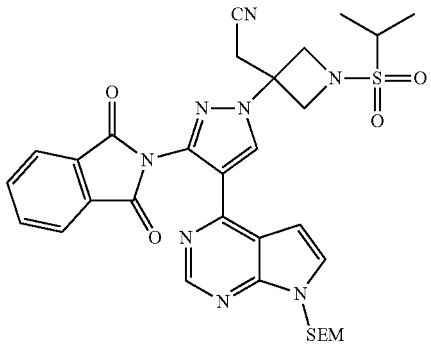 [SMILES: CC(C)S(=O)(=O)N1CC(CC#N)(n2cc(-c3ncnc4c3ccn4COCC[Si](C)(C)C)c(N3C(=O)c4ccccc4C3=O)n2)C1]

To a 2 L reaction flask 78.5 g of tert-butyl 3-(cyanomethyl)-3-[3-(1,3-dioxoisoindolin-2-yl)-4-(7-{[2-(trimethylsilyl)ethoxy]methyl}-7H-pyrrolo[2,3-d]pyrimidin-4-yl)-1H-pyrazol-1-yl]azetidinyl-1-carboxylate (0.12 mol, 1.0 eq) and 800 mL of ethyl acetate were added under conditions of stirring at room temperature, and stirred to be dissolved. With controlling the temperature at 10-20° C., 150 ml of a solution of hydrogen chloride in tetrahydrofuran (0.60 mol, 5.0 eq) was added. The reaction was stirred overnight, and filtered. The resulting filter cake was transferred into a 1 L reaction flask, added with 350 mL of N,N-dimethylformamide, stirred, cooled down to 0-5° C., added with 38.0 g of triethylamine (0.38 mol, 3.0 eq), stirred for 30 min, followed by addition of 20.5 g of isopropylsulfonyl chloride (0.14 mol, 1.2 eq). After the addition was completed, the reaction was continued for 2 hours under the temperature control, and then stopped. The reaction solution was poured into 700 mL of water, and extracted with 2×500 mL of ethyl acetate. The organic phases were combined, and washed twice with water 2×300 mL. The liquids were separated, and the organic phase was dried and evaporated to dryness to obtain a light yellow solid weighed 57.0 g with a yield of 72.0%.

Step E: 2-{3-[3-amino-4-(7H-pyrrolo[2,3-d]pyrimidin-4-yl)-1H-pyrazol-1-yl]-1-(isopropylsulfonyl) azetidin-3-yl}acetonitrile

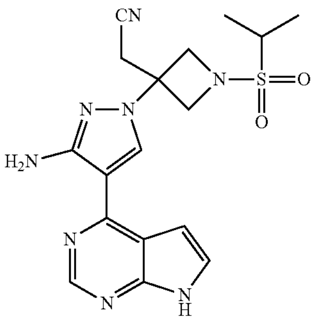

I

To a 1 L reaction flask 53.0 g of 2-{3-[3-(1,3-dioxoisoindolin-2-yl)-4-(7-{[2-(trimethylsilyl)ethoxy]methyl}-7H-pyrrolo[2,3-d]pyrimidin-4-yl)-1H-pyrazol-1-yl]-1-(isopropylsulfonyl)azetidin-3-yl}acetonitrile (0.08 mol, 1.0 eq) and 300 mL of acetonitrile were added, and 54.0 g of boron trifluoride diethyl etherate (0.24 mol, 3.0 eq) was slowly added dropwise, under stirring at room temperature. After the addition was completed, with rising the temperature to 40-50° C., the reaction was stirred for 3 h, and then stopped. The reaction solution was concentrated, and the residue was added with 300 mL of ethanol, stirred, and cooled down to room temperature. To the reaction system 38.5 g of ethylenediamine (0.64 mol, 8.0 eq) was added. After the addition was completed, the reaction was stirred for another 5 h, and then stopped. The reaction solution was poured into 500 mL of water, stirred and crystallized, and filtered. The filter cake was washed with addition of 200 mL, and filtered. The resulting solid was dried with air blast at 60° C. to constant weight. The weight was 28.3 g and the yield was 88.2%.

Example 4

Preparation of 2-{3-[3-amino-4-(7H-pyrrolo[2,3-d]pyrimidin-4-yl)-1H-pyrazol-1-yl]-1-(isopropylsulfonyl)azetidin-3-yl}acetonitrile (I)

Step A: 4-(7-{[2-(trimethylsilyl)ethoxy]methyl}-7H-pyrrolo[2,3-d]pyrimidin-4-yl)-1H-pyrazole-3-amine

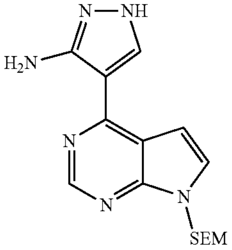 [SMILES: C[Si](C)(C)CCOCn1ccc2c(-c3c[nH]nc3N)ncnc21]

To a 10 L reaction flask 3.6 L of N,N-dimethylacetamide and 630 g of 3-amino-2-(7-{[2-(trimethylsilyl)ethoxy]methyl}-7H-pyrrolo[2,3-d]pyrimidin-4-yl)acrylonitrile (2.00 mol, 1.0 eq) were added under stirring at room temperature, stirred to be dissolved, followed by addition of 450 g of hydrazine hydrate (7.20 mol, 3.6 eq) and 240 g of N,N-dimethylformamide dimethyl acetal (2.00 mol, 1.0 eq). With rising the temperature to 80-90° C., the reaction was carried out for 6 h, and then stopped, and lowered to room temperature. The reaction solution was transferred into a 20 L transfer barrel, added with 7.5 L of water, stirred, solid precipitated, centrifuged and filtered. The filter cake was slurried with addition of 3.0 L of methyl tert-butyl ether, and filtered. The filter cake was dried at 55-60° C. to constant weight. The weight was 548 g and the yield was 83.0%.

Step B: 1-[4-(7-{[2-(trimethylsilyl)ethoxy]methyl}-7H-pyrrolo[2,3-d]pyrimidin-4-yl)-1H-pyrazol-3-yl] pyrrolidine-2,5-dione

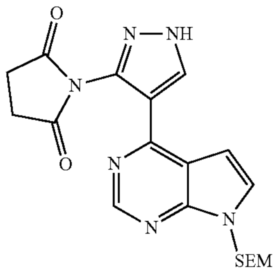 [SMILES: C[Si](C)(C)CCOCn1ccc2c(-c3c[nH]nc3N3C(=O)CCC3=O)ncnc21]

To a 3 L reaction flask 1.5 L of toluene, 166 g of 4-(7-{[2-(trimethylsilyl)ethoxy]methyl}-7H-pyrrolo[2,3-d] pyrimidin-4-yl)-1H-pyrazole-3-amine (0.50 mol, 1.0 eq), and 55.0 g of succinic anhydride (0.55 mol, 1.1 eq) were added under stirring at room temperature. A water separator was installed. The reaction system was heated to reflux, and reacted while separating water until there was no water to be separated, stopped heating, and cooled down. To the reaction system 600 mL of isopropyl ether was added, stirred and crystallized, and filtered. The resulting solid was dried, and weighted 176 g, with a yield of 85.0%.

Step C: 2-{3-[3-(2,5-dioxopyrrolidin-1-yl)-4-(7-{[2-(trimethylsilyl)ethoxy]methyl}-7H-pyrrolo[2,3-d] pyrimidin-4-yl)-1H-pyrazol-1-yl]-1-(isopropylsulfonyl)azetidin-3-yl}acetonitrile

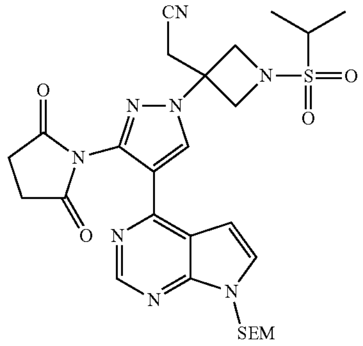 [SMILES: CC(C)S(=O)(=O)N1CC(CC#N)(n2cc(-c3ncnc4c3ccn4COCC[Si](C)(C)C)c(N3C(=O)CCC3=O)n2)C1]

To a 3 L reaction flask 124 g of 1-[4-(7-{[2-(trimethylsilyl)ethoxy]methyl}-7H-pyrrolo[2,3-d]pyrimidin-4-yl)-1H-pyrazol-3-yl]pyrrolidine-2,5-dione (0.30 mol, 1.0 eq), 4.60 g of DBU (0.03 mol, 0.1 eq), 1.8 L of acetonitrile and 66.0 g of 2-[1-(isopropylsulfonyl)azetidin-3-ylidene]acetonitrile (0.33 mol, 1.1 eq) were added under stirring at room temperature. With rising the temperature to 30-40° C., the reaction was stirred for 5 h, and then stopped, and filtered. The filtrate was concentrated, and the residue was added with 600 mL of isopropanol, stirred and crystallized, and filtered. The resulting solids were combined and dried. The weight was 172 g and the yield was 93.5%.

Step D: 2-(3-{3-(2,5-dioxopyrrolidin-1-yl)-4-[7-(hydroxymethyl)-7H-pyrrolo[2,3-d]pyrimidin-4-yl]-1H-pyrazol-1-yl}-1-(isopropylsulfonyl)azetidin-3-yl) acetonitrile

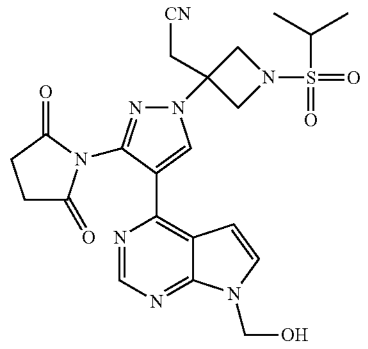 [SMILES: CC(C)S(=O)(=O)N1CC(CC#N)(n2cc(-c3ncnc4c3ccn4CO)c(N3C(=O)CCC3=O)n2)C1]

To a 2 L reaction flask 123 g of 2-{3-[3-(2,5-dioxopyrrolidin-1-yl)-4-(7H-pyrrolo[2,3-d]pyrimidin-4-yl)-1H-pyrazol-1-yl]-1-(isopropylsulfonyl)azetidin-3-yl}acetonitrile (0.20 mol, 1.0 eq) and 700 mL of acetonitrile were added, and stirred at room temperature. 136 g of boron trifluoride diethyl etherate (0.60 mol, 3.0 eq) was added dropwise. After the addition was completed, with rising the temperature to 40-50° C., the reaction was stirred for 5 h, and then stopped. The reaction solution was concentrated, and the residue was added with a saturated sodium carbonate solution to adjust pH=9-10, solid precipitated, stirred, and filtered. The filter cake was washed with 300 mL of water, and filtered. The filter cake was dried at 55-60° C. to obtain a light yellow solid weighed 92.5 g with a yield of 90.0%.

Step E: Preparation of 2-{3-[3-amino-4-(7H-pyrrolo[2,3-d]pyrimidin-4-yl)-1H-pyrazol-1-yl]-1-(isopropylsulfonyl azetidin-3-yl}acetonitrile (I)

I

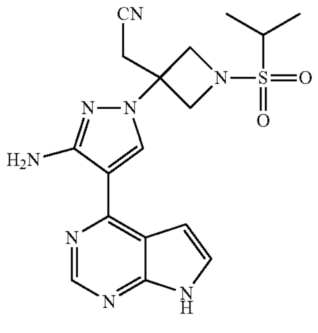

To a 2 L reaction flask 77.0 g of 2-(3-{3-(2,5-dioxopyrrolidin-1-yl)-4-[7-(hydroxymethyl)-7H-pyrrolo[2,3-d]pyrimidin-4-yl]-1H-pyrazol-1-yl}-1-(isopropylsulfonyl)azetidin-3-yl)acetonitrile (0.15 mol, 1.0 eq) and 800 ml of ethanol were added. 92.0 g of ethanolamine (1.50 mol, 10.0 eq) was added under stirring. The reaction system was heated to reflux and reacted for 8 h. The reaction was stopped, cooled, and filtered. The filter cake was added with 500 mL of water, stirred and crystallized, and filtered. The filter cake was dried at 55-60° C. to obtain a light yellow solid weighted 55.6 g with a yield of 92.4%.

Example 5

Preparation of 2-{3-[3-amino-4-(7H-pyrrolo[2,3-d]pyrimidin-4-yl)-1H-pyrazol-1-yl]-1-(isopropylsulfonyl)azetidin-3-yl}acetonitrile (I)

Step A: 2-[4-(7-{[2-(trimethylsilyl)ethoxy]methyl}-7H-pyrrolo[2,3-d]pyrimidin-4-yl)-1H-pyrazol-3-yl] isoindolinyl-1,3-dione

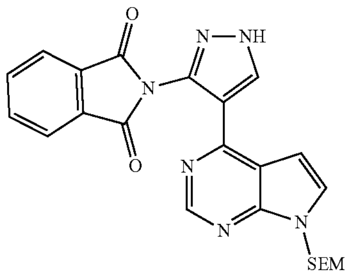 [SMILES: C[Si](C)(C)CCOCn1ccc2c(-c3c[nH]nc3N3C(=O)c4ccccc4C3=O)ncnc21]

To a 2 L reaction flask 600 mL of toluene, 82.5 g of 4-(7-{[2-(trimethylsilyl)ethoxy]methyl}-7H-pyrrolo[2,3-d]pyrimidin-4-yl)-1H-pyrazole-3-amine (0.25 mol, 1.0 eq), and 37.0 g of phthalic anhydride (0.25 mol, 1.0 eq) were added under stirring at room temperature. The reaction system was heated to reflux, reacted while separating water until there was no water to be separated, stopped heating, cooled down and crystallized, and filtered. The filter cake was rinsed with a small amount of toluene, and filtered to obtain a solid, which was dried. The weight was 90.3 g and the yield was 78.5%.

Step B: 2-{3-[3-(1,3-dioxoisoindolin-2-yl)-4-(7-{[2-(trimethylsilyl)ethoxy]methyl}-7H-pyrrolo[2,3-d]pyrimidin-4-yl)-1H-pyrazol-1-yl]-1-(isopropylsulfonyl)azetidin-3-yl}acetonitrile

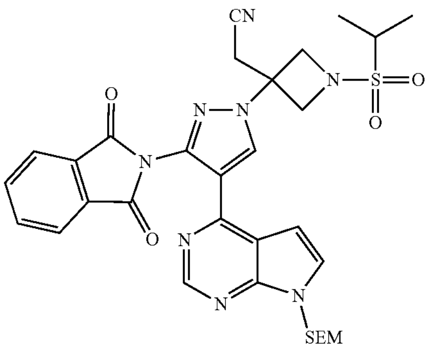 [SMILES: CC(C)S(=O)(=O)N1CC(CC#N)(n2cc(-c3ncnc4c3ccn4COCC[Si](C)(C)C)c(N3C(=O)c4ccccc4C3=O)n2)C1]

To a 2 L reaction flask 83.0 g of 2-[4-(7-{[2-(trimethylsilyl)ethoxy]methyl}-7H-pyrrolo[2,3-d]pyrimidin-4-yl)-1H-pyrazol-3-yl]isoindolinyl-1,3-dione (0.18 mol, 1.0 eq), 13.70 g of DBU (0.09 mol, 0.5 eq), 1.2 L of acetonitrile, and 40.0 g of 2-[1-(isopropylsulfonyl)azetidin-3-ylidene]acetonitrile (0.20 mol, 1.1 eq) were added under stirring at room temperature. The reaction was stirred at room temperature (25-30° C.) for 5 h, and then stopped. The reaction solution was concentrated, and the residue was added with 600 mL of isopropyl ether, stirred and crystallized, and filtered. The resulting solid was dried. The weight was 103 g and the yield was 86.6%.

Step C: Preparation of 2-{3-[3-amino-4-(7H-pyrrolo[2,3-d]pyrimidin-4-yl)-1H-pyrazol-1-yl]-1-(isopropylsulfonyl)azetidin-3-yl}acetonitrile (I)

I

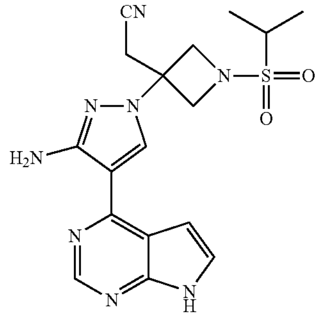

Under the conditions of stirring at room temperature, 92.5 g of 2-{3-[3-(1,3-dioxoisoindolin-2-)–4-(7-{[2-(trimethylsilyl)ethoxy]methyl}-7H-pyrrolo[2,3-d]pyrimidin-4-yl)-1H-pyrazol-1-yl]-1-(isopropylsulfonyl)azetidin-3-yl}acetonitrile (0.14 mol, 1.0 eq) and 500 mL of acetonitrile were added to a 1 L reaction flask, and stirred at room temperature. With controlling the temperature at 0-5° C., 65.0 g of boron trifluoride diethyl etherate (0.28 mol, 2.0 eq) was slowly added dropwise. After the addition was completed, the temperature was naturally raised to room temperature, and the reaction was stirred for another 5 h. The reaction was stopped, the reaction solution was concentrated, and the residue was added with 500 mL of ethanol, stirred, followed by addition of 44.0 g of hydrazine hydrate (0.70 mol, 5.0 eq), heated to reflux for 3 h, stopped heating, and cooled down naturally. The reaction solution was poured into 1.0 L of water, stirred and crystallized, filtered to obtain a light yellow solid. The weight was 43.3 g and the yield was 77.3%.

Example 6

Preparation of 2-{3-[3-amino-4-(7H-pyrrolo[2,3-d]pyrimidin-4-yl)-1H-pyrazol-1-yl]-1-(isopropylsulfonyl)azetidin-3-yl}acetonitrile (I)

Step A: 2-{3-[3-amino-4-(7-{[2-(trimethylsilyl)ethoxy]methyl}-7H-pyrrolo[2,3-d]pyrimidin-4-yl)-1H-pyrazol-1-yl]-1-(isopropylsulfonyl)azetidin-3-yl}acetonitrile

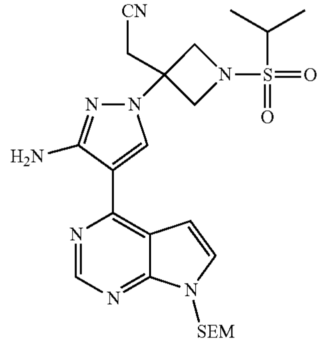 [SMILES: CC(C)S(=O)(=O)N1CC(CC#N)(n2cc(-c3ncnc4c3ccn4COCC[Si](C)(C)C)c(N)n2)C1]

To a 1 L reaction flask 400 mL of acetonitrile, 66.2 g of 4-(7-{[2-(trimethylsilyl)ethoxy]methyl}-7H-pyrrolo[2,3-d]pyrimidin-4-yl)-1H-pyrazole-3-amine (0.20 mol, 1.0 eq), 70.0 g of tetramethylguanidine (0.60 mol, 3.0 eq) and 44.0 g of 2-[1-(isopropylsulfonyl)azetidin-3-ylidene]acetonitrile (0.22 mol, 1.1 eq) were added under stirring at room temperature. After the addition was completed, with controlling the temperature at 45° C., the reaction was carried out overnight, and then stopped. The reaction solution was evaporated to dryness, acetonitrile was recovered, and the resulting residue was added with 300 mL of isopropanol, stirred and crystallized, and filtered to obtain a solid. The solid was rinsed by adding 100 mL of isopropanol, filtered, and the resulting solid was dried at 55° C. to constant weight. The weight was 83.2 g and the yield was 78.3%.

Step B: 2-{3-[3-(1,3-dioxoisoindolin-2-yl)-4-(7-{[2-(trimethylsilyl)ethoxy]methyl}-7H-pyrrolo[2,3-d]pyrimidin-4-yl)-1H-pyrazol-1-yl]-1-(isopropylsulfonyl)azetidin-3-yl}acetonitrile

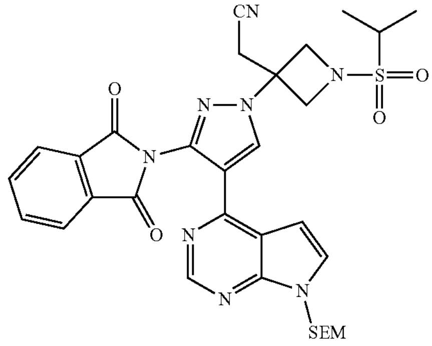 [SMILES: CC(C)S(=O)(=O)N1CC(CC#N)(n2cc(-c3ncnc4c3ccn4COCC[Si](C)(C)C)c(N3C(=O)c4ccccc4C3=O)n2)C1]

To a 1 L reaction flask 300 mL of toluene, 53.0 g of 2-{3-[3-amino-4-(7-{[2-(trimethylsilyl)ethoxy]methyl}-

7H-pyrrolo[2,3-d]pyrimidin-4-yl)-1H-pyrazol-1-yl]-1-(isopropylsulfonyl)azetidin-3-yl}acetonitrile (0.10 mol, 1.0 eq), and 15.0 g of phthalic anhydride (0.10 mol, 1.0 eq) were added under stirring at room temperature, stirred, and heated to 80° C. and reacted for 6 h. The reaction was stopped, cooled to room temperature, added with 300 mL of n-hexane, stirred and crystallized, and filtered. The resulting solid was dried. The weight was 57.8 g and the yield was 87.6%.

Step C: 2-(3-{3-(1,3-dioxoisoindolin-2-yl)-4-[7-(hydroxymethyl)-7H-pyrrolo[2,3-d]pyrimidin-4-yl]-1H-pyrazol-1-yl}-1-(isopropylsulfonyl)azetidin-3-yl) acetonitrile

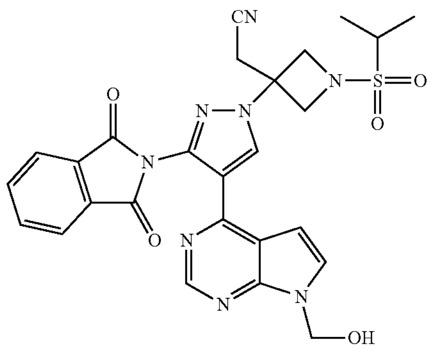 [SMILES: CC(C)S(=O)(=O)N1CC(CC#N)(n2cc(-c3ncnc4c3ccn4CO)c(N3C(=O)c4ccccc4C3=O)n2)C1]

To a 2 L reaction flask 53.0 g of 2-(3-(3-(1,3-dioxoisoindolin-2-yl)-4-(7-((2-(trimethylsilyl)ethoxy)methyl)-7H-pyrrolo[2,3-d]pyrimidin-4-yl)-1H-pyrazol-1-yl)-1-(isopropylsulfonyl)azetidin-3-yl)acetonitrile (0.08 mol, 1.0 eq), 400 mL of acetonitrile, and 90.5 g of boron trifluoride diethyl etherate (0.40 mol, 5.0 eq) were added under stirring at room temperature. After the addition was completed, with controlling the temperature at 45° C., the reaction was stirred for 5 h, and then stopped, and cooled to room temperature. The reaction system was added with a saturated sodium bicarbonate solution to adjust to neutral, solid precipitated, and filtered. The filter cake was rinsed with water. The resulting solid was dried with air blast at 55° C. to constant weight. The weight was 39.5 g and the yield was 87.8%.

1H NMR (400 MHz, DMSO-d6) δ 9.09 (s, 1H), 8.25 (s, 1H), 8.04-7.94 (m, 4H), 7.78 (d, J=3.7 Hz, 1H), 7.14 (d, J=3.7 Hz, 1H), 6.64 (t, J=7.3 Hz, 1H), 5.59 (d, J=7.3 Hz, 2H), 4.67 (d, J=9.1 Hz, 2H), 4.27 (d, J=9.1 Hz, 2H), 3.78 (s, 2H), 3.38 (m, J=6.8 Hz, 1H), 1.29 (d, J=6.8 Hz, 6H). HRMS (ESI): m/z=561.1663[M+1], C26H25N8O5S (Ion Formula).

Step D: 2-{3-[3-amino-4-(7H-pyrrolo[2,3-d]pyrimidin-4-yl)-1H-pyrazol-1-yl]-1-(isopropylsulfonyl) azetidin-3-yl}acetonitrile

I

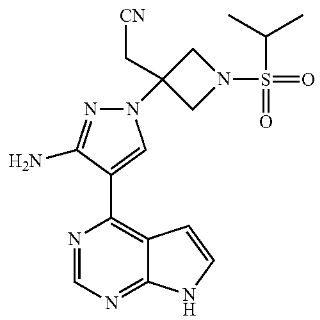

Under stirring at room temperature, to a 1 L reaction flask 33.7 g of 2-(3-(3-(1,3-dioxoisoindolin-2-yl)-4-(7-(hydroxymethyl)-7H-pyrrolo[2,3-d]pyrimidin-4-yl)-1H-pyrazol-1-yl)-1-(isopropylsulfonyl)azetidin-3-yl)acetonitrile (0.06 mol, 1.0 eq) and 300 mL of ethanol were added, stirred, and 84.0 g of ammonia water (0.6 mol, 10.0 eq) was added. After the addition was completed, the reaction was stirred for 10 h, and then stopped. The reaction solution was concentrated, and the residue was added with 300 mL of water, adjusted the pH of the aqueous phase to neutral by using 3N hydrochloric acid, stirred for 30 min, and filtered. The filter cake was washed with water to obtain a light yellow solid. 200 mL of methanol was added to the resulting solid, heated to reflux for 30 min, cooled, and filtered. The resulting solid was dried at 55° C. The weight was 19.8 g and the yield was 82.3%.

Example 7

Preparation of 2-{3-[3-amino-4-(7H-pyrrolo[2,3-d]pyrimidin-4-yl)-1H-pyrazol-1-yl]-1-(isopropylsulfonyl)azetidin-3-yl}acetonitrile (I)

Under the conditions of stirring at room temperature, to a 1 L reaction flask 300 mL of acetonitrile, 41.3 g of 1-[4-(7-{[2-(trimethylsilyl)ethoxy]methyl}-7H-pyrrolo[2,3-d]pyrimidin-4-yl)-1H-pyrazol-3-yl]pyrrolidine-2,5-dione (0.1 mol, 1.0 eq), and DBU3.00 (0.02 mol, 0.2 eq) were added, stirred for 30 min, and 22.0 g of 2-[1-(isopropylsulfonyl) azetidin-3-ylidene]acetonitrile (0.11 mol, 1.1 eq) was added. After the addition was completed, the reaction was stirred at room temperature for 4 h. Then 45.0 g of boron trifluoride diethyl etherate (0.20 mol, 2.0 eq) was added. After the addition was completed, the reaction was stirred for 3 h, and then stopped. The reaction solution was concentrated, and the residue was added with 500 mL of ethanol, and added with 37.0 g of ethanolamine (0.60 mol, 6.0 eq) under stirring, heated to reflux and reacted for 3 hours, stopped heating, and cooled down naturally. The reaction solution was poured into 1.5 L of water, stirred and crystallized, and filtered. The resulting solid was dried at 60° C. to constant weight. The weight was 29.2 g and the yield was 72.8%.

Example 8

Preparation of 2-{3-[3-amino-4-(7H-pyrrolo[2,3-d]pyrimidin-4-yl)-1H-pyrazol-1-yl]-1-(isopropylsulfonyl)azetidin-3-yl}acetonitrile (I)

Under the contions of stirring at room temperature, to a 2 L reaction flask 1.0 L of acetonitrile, 92.0 g of 2-[4-(7-{[2-(trimethylsilyl)ethoxy]methyl}-7H-pyrrolo[2,3-d]pyrimidin-4-yl)-1H-pyrazol-3-yl]isoindolinyl-1,3-dione (0.2 mol, 1.0 eq) and 15.0 g of DBU (0.10 mol, 0.5 eq) were added, stirred for 10 min, and 45.0 g of 2-[1-(isopropylsulfonyl)azetidin-3-ylidene]acetonitrile (0.22 mol, 1.1 eq) was added. After the addition was completed, with controlling the temperature at 45° C., the reaction was carried out for 4 h. To the reaction solution 90.0 g of boron trifluoride diethyl etherate (0.40 mol, 2.0 eq) was added. After the addition was completed, the reaction was stirred for 3 h, and then stopped. The reaction solution was concentrated, and the residue was added with LOL of ethanol, and added with 125 g of hydrazine hydrate (2.00 mol, 10.0 eq) under stirring, heated to reflux and reacted for 3 h, stopped heating, and cooled down naturally. The reaction solution was poured into 3.0 L of water, stirred and crystallized, and filtered. The resulting solid was dried at 60° C. to constant weight. The weigh was 52.6 g and the yield was 65.8%.

It should be noted by those skilled in the art that the embodiments described in the present invention are only exemplary, and various other substitutions, modifications and improvements can be made within the scope of the present invention. Therefore, the present invention is not limited to the above-described embodiments.

The invention claimed is:

1. A process for the preparation of a compound of formula 1:

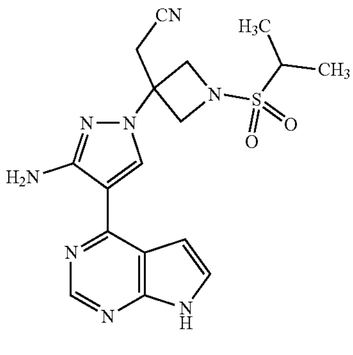

1 wherein the process comprises the following steps:

(1) reacting a compound of formula 2:

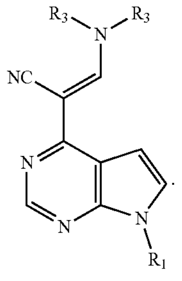

2 wherein:

$R_1$ is $CH_2OH$, $CH_2OCH_3$, $CH_2OC(CH_3)_3$ (Bum), $CH_2OCH_2$-phenyl (Bom), $C(O)OCH_2CCl_3$ (Troc), $CH_2OCH_2CH_2Si(CH_3)_3$ (SEM), $CH_2OC(O)C(CH_3)_3$(POM), $C(O)CH_3$, $C(O)CF_3$, $C(O)OCH_2$-phenyl (Cbz), $C(O)OCH_2CH_2Si(CH_3)_3$ (Teoc), $C(O)OCH_2CH_2S(O)_2$-(4-trifluoromethylphenyl) (TSC), $C(O)OC(CH_3)_3$(Boc), $C(O)OCH[C(CH_3)_2CH_3]_2$(Doc), C(O)O-(1-adamantyl) (Adoc), C(O)O-2-adamantyl (2-Adoc), C(phenyl)$_3$ (Tr), $Si(CH_3)_3$(Tms), Si(phenyl)$_3$ (Ts), $S(O)_2CH_3$, $S(O)_2CH_2CH_3$, $S(O)_2$phenyl, $S(O)_2$-p-toluene, $S(O)_2$-p-nitrophenyl, or 2-tetrahydropyranyl; and each $R_3$ is independently H or $C_1$-$C_4$ alkyl; or $R_3$ and $R_3$, together with the nitrogen atom to which they are attached, form a $C_3$- to $C_8$-membered ring;

with a hydrazine compound selected from the group consisting of a salt of hydrazine, an aqueous solution of hydrazine, and an organic solution of hydrazine, and optionally, an acetal selected from the group consisting of an N,N-di($C_1$-$C_4$ alkyl)formamide di($C_1$-$C_4$ alkyl) acetal and a 5- or 6-membered azaheterocycle-N-formamide di($C_1$-$C_4$ alkyl) acetal, to obtain a compound of formula 3:

3

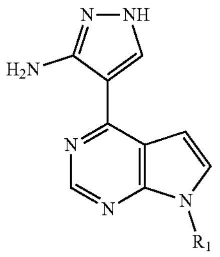

wherein:

$R_1$ is $CH_2OH$, $CH_2OCH_3$, $CH_2OC(CH_3)_3$ (Bum), $CH_2OCH_2$-phenyl (Bom), $C(O)OCH_2CCl_3$ (Troc), $CH_2OCH_2CH_2Si(CH_3)_3$ (SEM), $CH_2OC(O)C(CH_3)_3$(POM), $C(O)CH_3$, $C(O)CF_3$, $C(O)OCH_2$-phenyl (Cbz), $C(O)OCH_2CH_2Si(CH_3)_3$ (Teoc), $C(O)OCH_2CH_2S(O)_2$-(4-trifluoromethylphenyl) (TSC), $C(O)OC(CH_3)_3$(Boc), $C(O)OCH[C(CH_3)_2CH_3]_2$(Doc), C(O)O-(1-adamantyl) (Adoc), C(O)O-2-adamantyl (2-Adoc), C(phenyl)$_3$ (Tr), $Si(CH_3)_3$(Tms), Si(phenyl)$_3$ (Ts), $S(O)_2CH_3$, $S(O)_2CH_2CH_3$, $S(O)_2$phenyl, $S(O)_2$-p-toluene, $S(O)_2$-p-nitrophenyl, or 2-tetrahydropyranyl;

(2) reacting the compound of formula 3 obtained in step (1) above with a cyclic imide protecting agent selected from the group consisting of 1,2-cyclohexanedicarboxylic anhydride, glutaric anhydride, maleic anhydride, phthalic anhydride, 3,4-difluorophthalic anhydride, 3,6-difluorophthalic anhydride, 4-chlorophthalic anhydride, 3-methylphthalic anhydride, 4-methylphthalic anhydride, tetrahydrophthalic anhydride, 4-methyltetrahydrophthalic anhydride, 3,4-dimethylphthalic anhydride, 3-methoxyphthalic anhydride, 4-methoxyphthalic anhydride, methylhexahydrophthalic anhydride, succinic anhydride, methylsuccinic anhydride, 3,3-dimethylsuccinic anhydride, 3,4-dimethylsuccinic anhydride, and 3-bromotetrahydrofuran-2,5-dione, to obtain a compound of formula 3P:

3P

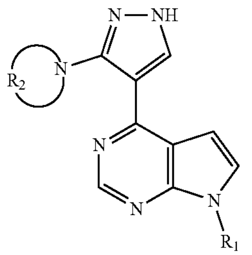

wherein:

$R_1$ is $CH_2OH$, $CH_2OCH_3$, $CH_2OC(CH_3)_3$ (Bum), $CH_2OCH_2$-phenyl (Bom), $C(O)OCH_2CCl_3$ (Troc), $CH_2OCH_2CH_2Si(CH_3)_3$ (SEM), $CH_2OC(O)C(CH_3)_3$(POM), $C(O)CH_3$, $C(O)CF_3$, C(O)$OCH_2$-phenyl (Cbz), $C(O)OCH_2CH_2Si(CH_3)_3$ (Teoc), $C(O)OCH_2CH_2S(O)_2$-(4-trifluoromethylphenyl) (TSC), $C(O)OC(CH_3)_3$(Boc), $C(O)OCH[C(CH_3)_2CH_3]_2$(Doc), C(O)O-(1-adamantyl) (Adoc), C(O)O-2-adamantyl (2-Adoc), C(phenyl)$_3$ (Tr), $Si(CH_3)_3$(Tms), Si(phenyl)$_3$ (Ts), $S(O)_2CH_3$, $S(O)_2CH_2CH_3$, $S(O)_2$phenyl, $S(O)_2$-p-toluene, $S(O)_2$-p-nitrophenyl, or 2-tetrahydropyranyl; and $R_2$, together with the intervening atoms and the nitrogen atom to which they are attached, form a cyclic imide protecting group selected from the group consisting of 1,2-cyclohexanedicarboximide, glutarimide, maleimide, phthalimide, 3,4-difluorophthalimide, 3,6-difluorophthalimide, 4-chlorophthalimide, 3-methylphthalimide, 4-methylphthalimide, 3,4-dimethylphthalimide, 3-methoxyphthalimide, 4-methoxyphthalimide, tetrahydrophthalimide, 4-methyltetrahydrophthalimide, methylhexahydrophthalimide, succinimide, 2-bromosuccinimide, methylsuccinimide, 2,2-dimethylsuccinimide, or 2,3-dimethylsuccinimide;

(3) reacting the compound of formula 3P obtained in step (2) above with a compound of formula SM2:

SM2

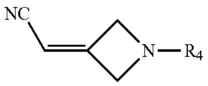

wherein:

$R_4$ is $CH_2OCH_3$, $CH_2OC(CH_3)_3$(Bum), $CH_2OCH_2$-phenyl (Bom), $C(O)OCH_2CCl_3$ (Troc), $CH_2OCH_2CH_2Si(CH_3)_3$(SEM), $CH_2OC(O)C(CH_3)_3$(POM), $C(O)CH_3$, $C(O)OCH_2$-phenyl (Cbz), $C(O)OCH_2CH_2Si(CH_3)_3$(Teoc), C(O)$OCH_2CH_2S(O)_2$-(4-trifluoromethylphenyl) (TSC), $C(O)OC(CH_3)_3$(Boc), $C(O)OCH[C(CH_3)_2CH_3]_2$(Doc), C(O)O-(1-adamantyl) (Adoc), C(O)O-2-adamantyl (2-Adoc), C(phenyl)$_3$ (Tr), $Si(CH_3)_3$(Tms), Si(phenyl)$_3$ (Ts), $S(O)_2CH_3$, $S(O)_2CH_2CH_3$, $S(O)_2$phenyl, $S(O)_2$-p-toluene, $S(O)_2$-p-nitrophenyl, or 2-tetrahydropyranyl (THP);

in the presence of a base selected from the group consisting of sodium hydroxide, potassium hydroxide, sodium carbonate, potassium carbonate, cesium carbonate, sodium methoxide, potassium methoxide, sodium hydride, sodium tert-butoxide, potassium tert-butoxide, tetramethylguanidine, triethylamine, diisopropylethylamine, 1,8-diazabicyclo[5.4.0]undec-7-ene (DBU), 1,5-diazabicyclo[4.3.0]non-5-ene (DBN), 1,5,7-triazabicyclo[4.4.0]dec-5-ene (TBD), and 7-methyl-1,5,7-triazabicyclo[4.4.0]dec-5-ene (MTBD), to obtain a compound of formula 4P1:

4P1

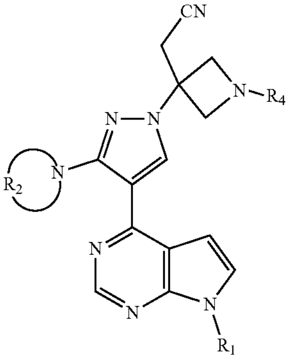

wherein:

$R_1$ is $CH_2OH$, $CH_2OCH_3$, $CH_2OC(CH_3)_3$ (Bum), $CH_2OCH_2$-phenyl (Bom), $C(O)OCH_2CCl_3$ (Troc), $CH_2OCH_2CH_2Si(CH_3)_3$ (SEM), $CH_2OC(O)C(CH_3)_3$(POM), $C(O)CH_3$, $C(O)CF_3$, C(O)$OCH_2$-phenyl (Cbz), $C(O)OCH_2CH_2Si(CH_3)_3$ (Teoc), $C(O)OCH_2CH_2S(O)_2$-(4-trifluoromethylphenyl) (TSC), $C(O)OC(CH_3)_3$(Boc), C(O)$OCH[C(CH_3)_2CH_3]_2$(Doc), C(O)O-(1-adamantyl) (Adoc), C(O)O-2-adamantyl (2-Adoc), C(phenyl)$_3$ (Tr), $Si(CH_3)_3$(Tms), Si(phenyl)$_3$ (Ts), $S(O)_2CH_3$, $S(O)_2CH_2CH_3$, $S(O)_2$phenyl, $S(O)_2$-p-toluene, $S(O)_2$-p-nitrophenyl, or 2-tetrahydropyranyl; and $R_2$, together with the intervening atoms and the nitrogen atom to which they are attached, form a cyclic imide protecting group selected from the group consisting of 1,2-cyclohexanedicarboximide, glutarimide, maleimide, phthalimide, 3,4-difluorophthalimide, 3,6-difluorophthalimide, 4-chlorophthalimide, 3-methylphthalimide, 4-methylphthalimide, 3,4-dimethylphthalimide, 3-methoxyphthalimide, 4-methoxyphthalimide, tetrahydrophthalimide, 4-methyltetrahydrophthalimide, methylhexahydrophthalimide, succinimide, 2-bromosuccinimide, methylsuccinimide, 2,2-dimethylsuccinimide, or 2,3-dimethylsuccinimide; and $R_4$ is $CH_2OCH_3$, $CH_2OC(CH_3)_3$(Bum), $CH_2OCH_2$-phenyl (Bom), $C(O)OCH_2CCl_3$ (Troc), $CH_2OCH_2CH_2Si(CH_3)_3$(SEM), $CH_2OC(O)C(CH_3)_3$(POM), $C(O)CH_3$, $C(O)OCH_2$-phenyl (Cbz), $C(O)OCH_2CH_2Si(CH_3)_3$(Teoc), C(O)$OCH_2CH_2S(O)_2$-(4-trifluoromethylphenyl) (TSC), $C(O)OC(CH_3)_3$(Boc), $C(O)OCH[C(CH_3)_2CH_3]_2$(Doc), C(O)O-(1-adamantyl) (Adoc), C(O)O-2-adamantyl (2-Adoc), C(phenyl)$_3$ (Tr), $Si(CH_3)_3$(Tms), Si(phenyl)$_3$ (Ts), $S(O)_2CH_3$, $S(O)_2CH_2CH_3$, $S(O)_2$phenyl, $S(O)_2$-p-toluene, $S(O)_2$-p-nitrophenyl, or 2-tetrahydropyranyl (THP);

(4) reacting the compound of formula 4P1 obtained in step (3) above with a mineral acid or an organic acid, to obtain a compound of formula 5:

5

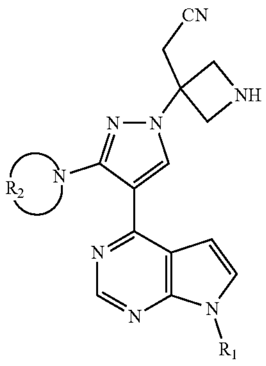

or a salt thereof, wherein:

$R_1$ is $CH_2OH$, $CH_2OCH_3$, $CH_2OC(CH_3)_3$ (Bum), $CH_2OCH_2$-phenyl (Bom), $C(O)OCH_2CCl_3$ (Troc), $CH_2OCH_2CH_2Si(CH_3)_3$ (SEM), $CH_2OC(O)C(CH_3)_3$(POM), $C(O)CH_3$, $C(O)CF_3$, C(O)$OCH_2$-phenyl (Cbz), $C(O)OCH_2CH_2Si(CH_3)_3$ (Teoc), $C(O)OCH_2CH_2S(O)_2$-(4-trifluoromethylphenyl) (TSC), $C(O)OC(CH_3)_3$(Boc), C(O)$OCH[C(CH_3)_2CH_3]_2$(Doc), C(O)O-(1-adamantyl) (Adoc), C(O)O-2-adamantyl (2-Adoc), C(phenyl)$_3$ (Tr), $Si(CH_3)_3$(Tms), Si(phenyl)$_3$ (Ts), $S(O)_2CH_3$, $S(O)_2CH_2CH_3$, $S(O)_2$phenyl, $S(O)_2$-p-toluene, $S(O)_2$-p-nitrophenyl, or 2-tetrahydropyranyl; and $R_2$, together with the intervening atoms and the nitrogen atom to which they are attached, form a cyclic imide protecting group selected from the group consisting of 1,2-cyclohexanedicarboximide, glutarimide, maleimide, phthalimide, 3,4-difluorophthalimide, 3,6-difluorophthalimide, 4-chlorophthalimide, 3-methylphthalimide, 4-methylphthalimide, 3,4-dimethylphthalimide, 3-methoxyphthalimide, 4-methoxyphthalimide, tetrahydrophthalimide, 4-methyltetrahydrophthalimide, methylhexahydrophthalimide, succinimide, 2-bromosuccinimide, methylsuccinimide, 2,2-dimethylsuccinimide, or 2,3-dimethylsuccinimide;

(5) reacting the compound of formula 5 obtained in step (4) above, or a salt thereof, with an isopropylsulfonyl reagent selected from the group consisting of $ClS(O)_2CH(CH_3)_2$, $BrS(O)_2CH(CH_3)_2$, $HOS(O)_2CH(CH_3)_2$, $CH_3OS(O)_2CH(CH_3)_2$, $CH_3CH_2OS(O)_2CH(CH_3)_2$, and $(CH_3)_2CHOS(O)_2CH(CH_3)_2$, to obtain a compound of formula 4P2:

4P2

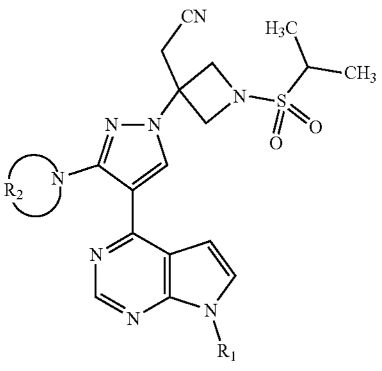

wherein:

$R_1$ is $CH_2OH$, $CH_2OCH_3$, $CH_2OC(CH_3)_3$ (Bum), $CH_2OCH_2$-phenyl (Bom), $C(O)OCH_2CCl_3$ (Troc), $CH_2OCH_2CH_2Si(CH_3)_3$ (SEM), $CH_2OC(O)C(CH_3)_3$ (POM), $C(O)CH_3$, $C(O)CF_3$, C(O)$OCH_2$-phenyl (Cbz), $C(O)OCH_2CH_2Si(CH_3)_3$ (Teoc), $C(O)OCH_2CH_2S(O)_2$-(4-trifluoromethylphenyl) (TSC), $C(O)OC(CH_3)_3$(Boc), C(O)$OCH[C(CH_3)_2CH_3]_2$(Doc), C(O)O-(1-adamantyl) (Adoc), C(O)O-2-adamantyl (2-Adoc), C(phenyl)$_3$ (Tr), $Si(CH_3)_3$(Tms), Si(phenyl)$_3$ (Ts), $S(O)_2CH_3$, $S(O)_2CH_2CH_3$, $S(O)_2$phenyl, $S(O)_2$-p-toluene, $S(O)_2$-p-nitrophenyl, or 2-tetrahydropyranyl; and $R_2$, together with the intervening atoms and the nitrogen atom to which they are attached, form a cyclic imide protecting group selected from the group consisting of 1,2-cyclohexanedicarboximide, glutarimide, maleimide, phthalimide, 3,4-difluorophthalimide, 3,6-difluorophthalimide, 4-chlorophthalimide, 3-methylphthalimide, 4-methylphthalimide, 3,4-dimethylphthalimide, 3-methoxyphthalimide, 4-methoxyphthalimide, tetrahydrophthalimide, 4-methyltetrahydrophthalimide, methylhexahydrophthalimide, succinimide, 2-bromosuccinimide, methylsuccinimide, 2,2-dimethylsuccinimide, or 2,3-dimethylsuccinimide;

(6) reacting the compound of formula 4P2 obtained in step (5) above with a reagent selected from the group consisting of trifluoroacetic acid, trifluoromethanesulfonic acid, boron trifluoride, lithium tetrafluoroborate, sodium tetrafluoroborate, and potassium tetrafluoroborate, to obtain a compound of formula 6:

6

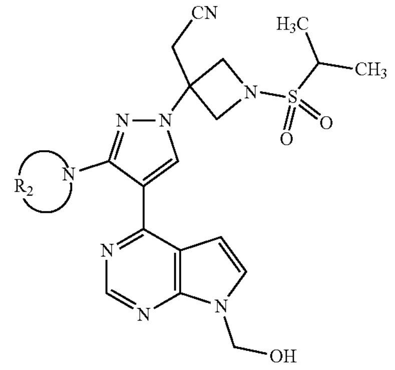

wherein:

$R_2$, together with the intervening atoms and the nitrogen atom to which they are attached, form a cyclic imide protecting group selected from the group consisting of 1,2-cyclohexanedicarboximide, glutarimide, maleimide, phthalimide, 3,4-difluorophthalimide, 3,6-difluorophthalimide, 4-chlorophthalimide, 3-methylphthalimide, 4-methylphthalimide, 3,4-dimethylphthalimide, 3-methoxyphthalimide, 4-methoxyphthalimide, tetrahydrophthalimide, 4-methyltetrahydrophthalimide, methylhexahydrophthalimide, succinimide, 2-bromosuccinimide, methylsuccinimide, 2,2-dimethylsuccinimide, or 2,3-dimethylsuccinimide; and (7) reacting the compound of formula 6 obtained in step (6) above with an elimination reagent selected from the group consisting of ammonia gas, ammonia water, ethylenediamine, propylenediamine, ethanolamine, propanolamine, hydrazine, hydrazine hydrate, a hydrazine salt, and an organic solution of hydrazine, or a combination thereof, to obtain the compound of formula 1:

1

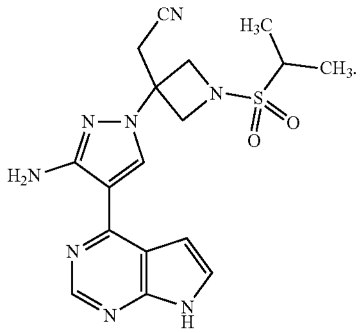

2. The process according to claim 1, wherein in step (1), the acetal is selected from the group consisting of pyrrolidine-N-formamide diethyl acetal, piperidine-N-formamide dimethyl acetal, piperidine-N-formamide diethyl acetal, morpholine-N-formamide dimethyl acetal, and morpholine-N-formamide diethyl acetal.

* * * * *